US011150209B2

(12) United States Patent
Yungers et al.

(10) Patent No.: US 11,150,209 B2
(45) Date of Patent: Oct. 19, 2021

(54) VERIFYING STRUCTURAL INTEGRITY OF MATERIALS USING ELECTRICAL PROPERTIES

(71) Applicant: 3M INNOVATIVE PROPERTIES COMPANY, St. Paul, MN (US)

(72) Inventors: Christopher R. Yungers, Saint Paul, MN (US); David H. Redinger, Afton, MN (US); Eric M. Chinnock, Chanhassen, MN (US); Jennifer F. Schumacher, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 4 days.

(21) Appl. No.: 16/626,264

(22) PCT Filed: Jun. 29, 2018

(86) PCT No.: PCT/IB2018/054868
§ 371 (c)(1),
(2) Date: Dec. 23, 2019

(87) PCT Pub. No.: WO2019/003208
PCT Pub. Date: Jan. 3, 2019

(65) Prior Publication Data
US 2020/0116661 A1    Apr. 16, 2020

Related U.S. Application Data

(60) Provisional application No. 62/527,663, filed on Jun. 30, 2017.

(51) Int. Cl.
*G01N 27/20* (2006.01)
(52) U.S. Cl.
CPC .................. *G01N 27/20* (2013.01)

(58) Field of Classification Search
CPC ................................. G01N 27/025
See application file for complete search history.

(56) References Cited

U.S. PATENT DOCUMENTS

| 4,914,378 A | 4/1990 | Hayashi |
| 2004/0061510 A1* | 4/2004 | Hands .................. G01N 27/20 |
| | | 324/700 |

(Continued)

FOREIGN PATENT DOCUMENTS

WO    WO 2013-086626    6/2013

OTHER PUBLICATIONS

Frias et al. ("Electrical Resistance Tomography with Voltage Excitation", Conference Paper, May 2016, doi: 10.1109/I2MTC.2016.7520444) (Year: 2016).*

(Continued)

*Primary Examiner* — Jennifer Bahls
(74) *Attorney, Agent, or Firm* — Sriram Srinivasan; Thomas M. Spielbauer

(57) ABSTRACT

A measurement system may include an electrical signal source; a plurality of electrical contacts electrically coupled to a tested material; a respective resistor associated with each electrical contact; a common node to which the respective resistors are electrically connected; and a control module. The control module may cause the electrical signal source to be electrically connected to a selected electrical contact as an input electrical contact. The remaining electrical contacts are electrically connected to a return node of the electrical signal source as extraction electrical contacts. The control module also may cause the electrical signal source to output an electrical signal to an input electrical contact; cause a respective electrical signal parameter to be determined at the respective resistor associated with each respective extraction electrical contact; and determine (Continued)

whether the tested material includes a crack or other defect based on the respective electrical signal parameters.

17 Claims, 9 Drawing Sheets

(56) References Cited

U.S. PATENT DOCUMENTS

| | | | |
|---|---|---|---|
| 2011/0163770 A1* | 7/2011 | Mahalingam | G01N 33/2823 |
| | | | 324/693 |
| 2012/0235693 A1 | 9/2012 | Feng | |
| 2013/0197891 A1* | 8/2013 | Jessop | G01V 3/081 |
| | | | 703/9 |
| 2018/0374244 A1* | 12/2018 | Borbas | G01R 27/04 |

OTHER PUBLICATIONS

Liu, "Electrical Resistance Tomography based on the Single Drive Electrode Method", IEEE, Proceedings of the Third International Conference on Machine Learning and Cybernetics Shanghai, Aug. 26-29, 2004, vol. 1, pp. 632-637, XP010760438.

International Search Report for PCT International Application No. PCT/IB2018/054868, dated Oct. 11, 2018, 5pgs.

* cited by examiner

VERIFYING STRUCTURAL INTEGRITY OF MATERIALS USING ELECTRICAL PROPERTIES

CROSS REFERENCE TO RELATED APPLICATIONS

This application is a national stage filing under 35 U.S.C. 371 of PCT/IB2018/054868, filed Jun. 29, 2018, which claims the benefit of Provisional Application No. 62/527,663, filed Jun. 30, 2017, the disclosure of which is incorporated by reference in their entirety herein.

TECHNICAL FIELD

The disclosure relates to techniques for verifying structural integrity of conductive or semiconductive materials.

BACKGROUND

Many materials are useful when their mechanical properties remain intact, but less useful when damaged, such as when cracked. Thus, detection of whether these materials are damaged is important. As one example, ceramic body plating is used to protect soldiers, police officers, and other security personnel from projectiles. Ceramic body plating may be useful when undamaged, but may be replaced after being damaged, e.g., after cracking.

X-ray scanning, including X-ray radiography and X-ray computed tomography (CT scanning) may be used to detect cracks or other defects in materials. However, such techniques may utilize large and heavy scanners, which may not be easily portable. Further, X-ray scanning and X-ray CT scanning may be relatively expensive, relatively slow, or both.

SUMMARY

In some examples, the disclosure describes a measurement system that includes an electrical signal source; a plurality of electrical contacts electrically coupled to a tested material; a respective resistor associated with each electrical contact; a common node to which the respective resistors are electrically connected; and a control module. The control module may be configured to cause the electrical signal source to be electrically connected to a selected electrical contact of the plurality of electrical contacts as an input electrical contact. The remaining electrical contacts of the plurality of electrical contacts are electrically connected to a return node of the electrical signal source as extraction electrical contacts. The control module also may be configured to cause the electrical signal source to output an electrical signal to the input electrical contact; cause a respective electrical signal parameter to be determined at the respective resistor associated with each respective extraction electrical contact; and determine whether the tested material includes a crack or other defect based on the respective electrical signal parameters.

In some examples, the disclosure describes a method that includes causing, by a control module, an electrical signal source to be electrically connected to a selected electrical contact of a plurality of electrical contacts as an input electrical contact. The remaining electrical contacts of the plurality of electrical contacts are electrically connected to a return node of the electrical signal source as extraction electrical contacts. The method also may include causing, by the control module, the electrical signal source to output an electrical signal to the input electrical contact; causing, by the control module, a respective electrical signal parameter to be determined at a respective resistor associated with each respective extraction electrical contact. The respective resistors may be electrically connected to a common node that is between the respective resistors and the return node. The method also may include determining, by the control module, whether the tested material includes a crack or other defect based on the respective electrical signal parameters.

In some examples, the disclosure describes a computer-readable medium that includes instructions that, when executed by one or more processors, causes the one or more processors to cause an electrical signal source to be electrically connected to a selected electrical contact of a plurality of electrical contacts as an input electrical contact. The remaining electrical contacts of the plurality of electrical contacts are electrically connected to a return node of the electrical signal source as extraction electrical contacts. The computer-readable medium also may include instructions that, when executed by the one or more processors, causes the one or more processors to cause the electrical signal source to output an electrical signal to the input electrical contact and cause a respective electrical signal parameter to be determined at a respective resistor associated with each respective extraction electrical contact. The respective resistors may be electrically connected to a common node that is between the respective resistors and the return node. The computer-readable medium further may include instructions that, when executed by the one or more processors, causes the one or more processors to determine whether the tested material includes a crack or other defect based on the respective electrical signal parameters.

The techniques described herein may provide one or more advantages. For example, using a measurement system that utilizes a voltage source to provide the electrical signal used to test the tested material may reduce cost of the measurement system compared to a measurement system that utilizes a current source, as current sources often are more expensive than voltage sources. Additionally, many microcontrollers include built-in voltage sources. Further, by measuring voltage drops across respective resistors between the respective extraction electrical contacts and the common node while the electrical signal source is outputting the electrical signal to the input electrical contact may allow use of simpler electrical pathways, e.g., simpler switches for selecting electrical contacts. Further, in some examples, a measurement system may include a summing resistor between the respective resistors and the power supply return node, which allows determination of a total current. By determining a respective ratio between each respective electrical parameter (e.g., current) associated with each respective resistor and the electrical parameter (e.g., current) determined using the summing resistor, the respective electrical parameters may be normalized, allowing measurements to be compared between electrical signal sources or testing instances. This may facilitate use of data determined during a separate testing instance, such as control data representing an intact testing material, to determine whether the tested material includes a crack or other defect. This may also reduce or eliminate temperature effects on the measurement of the electrical signal parameters. Further, a measurement system as described herein may offer improved portability and cost compared to an X-ray radiography or X-ray computed tomography system, while offering sufficient accuracy and detail to enable detection of cracks or other defects in a material being used in the field.

The details of one or more examples are set forth in the accompanying drawings and the description below. Other features, objects, and advantages will be apparent from the description and drawings, and from the claims.

DETAILED DESCRIPTION

Figure 1:
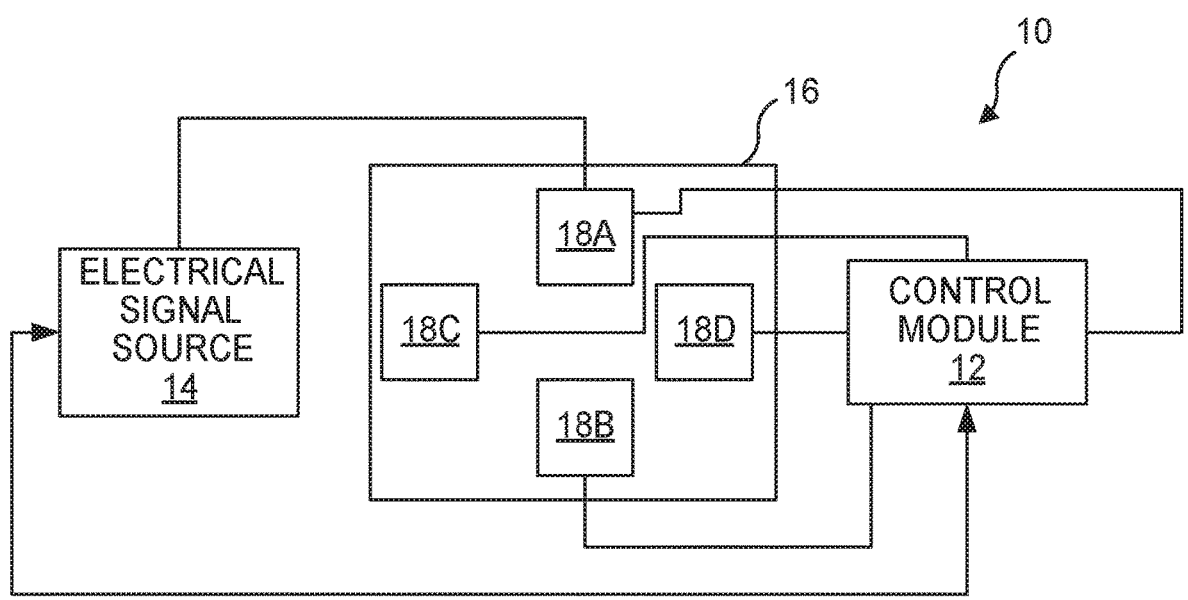
FIGS. 1 and 2 are a conceptual and schematic block diagrams illustrating example measurement systems for determining whether a tested material includes a crack or other defect.

The disclosure describes measurement systems and techniques for verifying structural integrity of a tested material, in which the measurement system includes a control module, an electrical signal source, and a plurality of electrical contacts. Each electrical contact of the plurality of electrical contacts is connected to a common node via a respective resistor. The control module may cause one electrical contact of the plurality of electrical contacts to be electrically connected to the electrical signal source as an input electrical contact, where the remaining electrical contacts are electrically connected to a return node of the electrical signal source as extraction electrical contacts. In some examples, the input electrical contact additionally may be electrically connected to the common node. In this way, the electrical signal may be extracted from the tested material via the remaining electrical contacts in parallel.

The control module may cause the electrical signal source to output an electrical signal, and, while the current is being extracted through the extraction electrical contacts, may measure an electrical signal parameter associated with each of the extraction electrical contacts. While the electrical signal source is outputting the electrical signal to the input electrical contact, the control module may cause a respective voltage drop associated each respective resistor to be measured, e.g., by an analog-to-digital converter.

The control module may determine whether the tested material includes a crack or other defect based on the respective electrical signal parameters (e.g., respective voltage drops or currents determined using the voltage drop and the resistance of the respective resistor). For example, the control module may utilize the respective electrical signal parameters and control electrical signal parameters to determine whether the material includes a crack or other defect. Each control electrical signal parameter may be associated with the same input electrical contact and the same extraction electrical contact as a corresponding electrical signal parameter and may have been measured at a time at which it was independently known that the tested material was intact (i.e., without a crack or other defect).

As another example, the control module may utilize a first electrical signal parameter associated with a first extraction electrical contact and a second electrical signal parameter associated with a second extraction electrical contact. The control module may determine a ratio between the first and second electrical signal parameters and determine whether the tested material includes a crack or other defect based on the ratio, or may compare the ratio to a control ratio. The control ratio may be associated with the same input electrical contact and the same extraction electrical contacts as the ratio and have been determined at a time at which it was independently known that the tested material was intact (i.e., without a crack or other defect).

As an additional example, the positions of the contact between at least two electrical contacts on the tested material may be selected to allow meaningful comparisons between the first and second measured electrical signal parameters. For example, electrical contacts may be positioned on the tested material based on a symmetry of the tested material, so that each measured electrical signal parameter is substantially the same when the material is intact, or both.

In some examples, the measurement system may include a summing resistor electrically connected between the common node and the return node of the electrical signal source. As the summing resistor is electrically connected after the common node into which all conductors from the respective resistors are connected, all electrical current from the tested material conducts through the summing resistor. The control module may cause a voltage across the summing resistor to be measured to determine a reference current. The control module may determine a respective ratio of each electrical signal parameter (e.g., current) to the reference current, and may utilize the respective ratios in any of the techniques described herein to determine whether the tested material includes a crack or other defect. By determining ratios of the electrical signal parameters to the reference current, effects of changes in impedance of the tested material due to changes in temperature may be reduced or substantially eliminated.

By utilizing measurement systems as described herein, circuitry may be relatively simple. For example, the electrical signal source may include a voltage source instead of a current source. A voltage source may be less expensive than a current source. The summing resistor may allow determination of the current through the tested material, even when a voltage source is utilized. Further, by using a single input electrical contact and connecting the remaining electrical contacts to a common node, switching circuitry (e.g., a switch network or programmable switch array) may be simpler than other measurement systems utilizing other measurement techniques.

Additionally, the measurement systems may be relatively smaller, more portable, and less expensive than other systems used to detect cracks in a material. For example, X-ray radiography or X-ray computed tomography (CT) may be used to detect cracks in a material, but utilize relatively large, relatively expensive equipment to perform the crack detection. This may prevent X-ray radiography and X-ray CT from being portable, such as being used to test materials in the environments in which they are used. Moreover, X-ray radiography and X-ray CT may be relatively time consuming. In contrast, the systems and techniques described herein utilize relatively smaller, relatively less expensive equipment.

FIG. 1 is conceptual and schematic block diagram illustrating an example measurement system 10 for determining whether a tested material 16 includes a crack or other defect. Measurement system 10 of FIG. 1 includes a control module 12, an electrical signal source 14, and a plurality of electrical contacts 18A-18D (collectively, "electrical contacts 18"). Electrical contacts 18 are electrically coupled to tested material 16, which is being tested using measurement system 10 for the presence of a crack or other defect.

Tested material 16 may include any material for which detection of a potential crack or other defect is desired. In some examples, tested material 16 may be an electrically conductive or an electrically semiconductive material. For example, tested material 16 may include a metal, an alloy, a metalloid, a semiconductor, an electrically conductive or semiconductive ceramic, or the like. In some examples, tested material 16 may include a ceramic such as boron carbide ($B_4C$), silicon carbide (SiC), alumina ($Al_2O_3$), composites thereof, or the like.

Tested material 16 may be used in any one of a wide variety of applications. For example, tested material 16 may be a ceramic that has relatively high hardness, a relatively high Young's modulus, a relatively high tensile strength, and may be used in ceramic armor plating. Ceramic armor plating may be used in body armor for military and police personnel, vehicle armor, or the like. Example materials for ceramic armor plating include boron carbide ($B_4C$), silicon carbide (SiC), alumina ($Al_2O_3$), composites thereof, or the like.

Tested material 16 may define any geometry, and the geometry of tested material 16 may be based at least in part on the intended use for tested material 16. For example, ceramic armor plating may have a geometry defined by the surface that the armor plating will be applied to. Example geometries for tested material 16 include, but are not limited to, polygonal solids, such as rectangular solids or solids with more sides. In some examples, tested material 16 includes a symmetry. As used herein, a symmetry may include, for example, a line, a plane, a curve, or a manifold for which a single mathematical operation made with reference to the symmetry maps each point or volume of tested material 16 to another point or volume of tested material 16. Tested material 16 may include two-dimensional symmetry, three-dimensional symmetry, or no symmetry.

Electrical signal source 14 may include any device configured to output an electrical signal to electrical contacts 18. The electrical signal may include an alternating current (AC) signal or a direct current (DC) signal. In some examples, electrical signal source 14 may include a current source configured to output a current signal; in other examples, electrical signal source 14 may include a voltage source configured to output a voltage signal. In some examples, a voltage source may be preferred, as a voltage source may be less expensive than a current source. Electrical signal source 14 may include, for example, a power source, such as a battery, a capacitor, a supercapacitor, a transformer electrically connected to a mains voltage, or the like. In some examples, in addition to the power source, electrical signal source 14 may include analog or digital circuitry configured to receive the electrical signal from the power source and modify the electrical signal into a format suitable for output to electrical contacts 18.

Electrical contacts 18 include a plurality of electrical contacts electrically coupled to tested material 16. In some examples, as shown in FIG. 1, electrical contacts 18 may include a first electrical contact 18A electrically connected to electrical signal source 14 as an input electrical contact, e.g., by a lead wire. Electrical contacts 18 also may include the remaining electrical contacts 18B-18D each electrically connected to control module 12 as an extraction electrical contact. Each of electrical contacts 18 may be electrically connected to tested material 16 using any suitable type of electrical connection, including, for example, an electrically conductive adhesive, an electrically conductive solder, embedding electrical contacts 18 in tested material 16, a dielectric coupling via capacitive coupling, or the like.

In some examples, as described below with respect to FIGS. 2, 4, and 5, electrical contacts 18 may include a plurality of electrical contacts connected to a switch network or a programmable switch array, which allows any electrical contact of the plurality of electrical contacts to be selectively coupled to electrical signal source 14 as an input electrical contact or to control module 12 or another device as an extraction electrical contact.

Electrical contacts 18 may be attached to any surface of tested material 16. The surface to which electrical contacts 18 are attached may affect the direction in which the electric field extends and current flows within tested material 16. Cracks or other defects may affect the magnitude of the voltage more significantly when the electrical field and current flow extends across a plane of the crack (e.g., normal to a surface of the crack). As such, in some examples, the likely locations of cracks or other defects and the likely orientation of cracks or other defects within tested material 16 may be predicted based on the use for tested material 16. In some of these examples, electrical contacts 18 may then be attached to tested material 16 so that the electrical field and current flow within tested material 16 extends substantially normal to a predicted orientation of the crack or other defect.

In some examples, rather than predicting a location of the crack or other defect within tested material 16 and placing electrical contacts 18 based on the prediction, electrical contacts 18 may be attached to more than one surface of tested material 16. For example, if tested material 16 is in the shape of a cube, electrical contacts 18 may be attached to three orthogonal surfaces of the cube. By attaching respective electrical contacts of electrical contacts 18 to three orthogonal surfaces, the electrical field and current flow may be caused to extend in one of three orthogonal directions depending on the electrical contacts 18 through which the electrical signal is applied. This may increase the likelihood that the electric field and current flow will extend within tested material 16 normal to the plane of any crack in tested material 16. Other examples are possible for other shapes.

In some examples, electrical contacts 18 may be positioned on tested material 16 according to a selected geometric relationship, to achieve a selected relationship between electrical signal parameters determined using electrical contacts 18, or both. For example, electrical contacts 18 may be positioned on tested material 16 so that each electrical contact of electrical contacts 18 is substantially symmetric to another one of electrical contacts 18 with reference to a symmetry of tested material 16. In some examples, one or more electrical contacts of electrical contacts 18 may be positioned on the symmetry of tested material 16.

Positioning electrical contacts 18 to be exactly symmetrical may be difficult to achieve in practice. Hence, electrical contacts 18 may be positioned to be substantially symmetrical. As used here, substantially symmetrical means that the electrical contacts 18 are placed approximately symmetrical with reference to a symmetry of tested material 16, e.g., within about 0.5 mm of being symmetric, within about 0.2 mm of being symmetric, or within about 0.1 mm of being symmetric.

In some examples, rather than electrical contacts 18 being positioned based on a symmetry of tested material 16, electrical contacts 18 may be positioned to achieve a selected relationship between electrical signal parameters determined using electrical contacts 18. For example, electrical contacts 18 may be positioned to achieve measurement of a substantially similar electrical signal parameter (e.g., the same or nearly the same voltage) in the absence of a crack or other defect.

In some examples, positioning electrical contacts 18 so that the electrical signal parameter associated with each respective electrical contact of electrical contacts 18 is exactly the same as the voltage measured using each other respective group of electrical contacts 18 may be difficult to achieve in practice. Hence, electrical contacts 18 may be positioned such that the electrical signal parameter associated with each respective group of electrical contacts 18 is substantially the same as the electrical signal parameter associated with each other respective group of electrical contacts 18 (for a selected input electrical contact). As used herein, substantially the same means that the electrical contacts are placed so that the voltage measured using each respective electrical contact of electrical contacts 18 is within a threshold amount as the electrical signal parameter associated with each other respective electrical contact of electrical contacts 18 in the absence of a crack or defect in tested material 16. The threshold amount may be a predetermined percentage of the measured voltage, such as, for example, 20%, 10%, 5%, or 1%.

In some examples, electrical contacts 18 may be positioned on tested material 16 to satisfy both symmetry and substantially equal measured voltages.

Control module 12 is configured to control operation of measurement system 10, including electrical signal source 14. Control module 12 may include any of a wide range of devices, including computer servers, desktop computers, notebook (i.e., laptop) computers, tablet computers, and the like. In some examples, computing device 12 may include a processor. The processor may include one or more microprocessors, digital signal processors (DSP), application specific integrated circuits (ASIC), field programmable gate arrays (FPGA), or other digital logic circuitry. In some examples, control module 12 may include an analog-to-digital converter (ADC), or measurement system 10 may include an ADC separate from computing device 12. In examples in which the ADC is separate from control module 12, the ADC may be electrically coupled between electrical contacts 18A-18D and control module 12. The ADC may measure an electrical signal parameter associated with each one of electrical contacts 18A-18D, e.g., under control of control module 12.

Control module 12 is electrically coupled to the extraction electrical contacts 18B-18D, and communicatively coupled to electrical signal source 14. Optionally, control module 12 also may be electrically coupled to input electrical contact 18A, as illustrated in FIG. 1. Control module 12 may be configured to cause electrical signal source 14 to output an electrical signal (e.g., a voltage signal or current signal) to input electrical contact 18A. Control module 12 also may be configured to determine an electrical signal parameter associated with each respective electrical contact of extraction electrical contacts 18B-18D in response to the electrical signal. In some examples, control module 12 also may be configured to determine an electrical signal parameter associated with input electrical contact 18A in response to the electrical signal. In some examples, control module 12 includes an ADC that measures the electrical signal parameter associated with each of extraction electrical contacts 18B-18D (and, optionally, input electrical contact 18A). In other examples, control module 12 controls an external ADC to measure the electrical signal parameter associated with each of extraction electrical contacts 18B-18D (and, optionally, input electrical contact 18A). In other examples, computing device 12 may measure or control another device to measure an electrical signal parameter (e.g., current). The electrical signal parameter may include, for example, a voltage (including a complex voltage, a real voltage, or an imaginary portion of the voltage) or a current, and may be measured at the respective extraction electrical contact or at a respective resistor associated with the respective extraction electrical contact (and, optionally, input electrical contact 18A).

To determine whether tested material 16 includes a crack or other defect, control module 12 may cause a first electrical contact, e.g., electrical contact 18A to be electrically connected to electrical signal source 14 as an input electrical signal. Control module 12 may control electrical signal source 14 to output an electrical signal (e.g., a voltage signal or a current signal) to input electrical signal contact 18A and measure an electrical signal parameter (e.g., a voltage) associated with each respective extraction electrical contact 18B-18D (and, optionally, input electrical contact 18A) while the electrical signal source 14 is outputting the electrical signal to input electrical signal contact 18A. In examples in which the voltage signal or current signal is a DC signal, the DC signal may include a positive or negative signal, such that positive current flows from input electrical contact 18A to extraction electrical contacts 18B-18D or positive current flows from extraction electrical contacts 18B-18D to input electrical contact 18A (e.g., negative current flows from input electrical contact 18A to extraction electrical contacts 18B-18D).

Control module 12 may then determine whether tested material 16 includes a crack or other defect based on the measured electrical signal parameters associated with each respective extraction electrical contact of extraction electrical contacts 18B-18D.

For example, control module 12 may compare each respective measured electrical signal parameter to a corresponding control electrical signal parameter. The control electrical signal parameter may be based on tested material 16, a model, or an average of a plurality of tested materials that are similar to or substantially the same as tested material 16. For example, control module 12 or another similar control module may determine the control electrical signal parameter at a time at which tested material 16 is manufactured, or a time at which an independent measurement (e.g., X-ray radiology or X-ray CT scan) may be used to verify that tested material 16 is intact, undamaged, or does not include a crack. Control module 12 or the other similar control module may determine the control electrical signal parameters by outputting the electrical signal to input electrical signal contact 18A and determining the control electrical signal parameters associated with each of extraction electrical contacts 18B-18D.

In other examples, the control electrical signal parameters may be determined using a model of the tested material in an intact (undamaged) state. For example, control module 12 may execute the model of tested material 16 and determine the control electrical signal parameters based on the model. In some examples, the model may include a physics-based model of the electrical properties of tested material 16, such as the physics-based model described below. In some other examples, the control electrical signal parameters may be determined as an average (e.g., mean) of a plurality of similar materials (e.g., in geometry and composition) that are known to be intact (undamaged). These control electrical signal parameters may be stored (e.g., in a memory device associated with control module 12) for later use.

Control module 12 then may compare the measured electrical signal parameters to the control electrical signal parameters. As one example, control module 12 may determine a difference or ratio between a respective magnitude of a respective measured electrical signal parameter and a respective magnitude of a respective control electrical signal parameter. Control module 12 then may compare this difference or ratio to a threshold electrical signal parameter value or ratio, and may determine that tested material 16 includes a crack or other defect in response to the difference being greater than the threshold voltage value. As another example, control module 12 may compare respective measured electrical signal parameters to a threshold electrical signal parameter range, and may determine that tested material 16 includes a crack or other defect in response to the measurement voltages being outside of the threshold electrical signal parameter range.

In some examples, rather than comparing respective measured electrical signal parameters to respective control electrical signal parameters, control module 12 may compare ratios of measured electrical signal parameters to ratios of control electrical signal parameters. For example, control module 12 may determine a ratio between a first measured electrical signal parameter associated with a first extraction electrical contact (e.g., electrical contact 18B) and a second measured electrical signal parameter associated with a second extraction electrical contact (e.g., electrical contact 18C), and may determine or have stored a ratio between a first control electrical signal parameter associated with the first extraction electrical contact (e.g., electrical contact 18B) and a second control electrical signal parameter associated with the second extraction electrical contact (e.g., electrical contact 18C). Control module 12 may determine a difference or ratio between the ratio of measured electrical signal parameters and the ratio of control electrical signal parameters. Control module 12 then may compare this difference or ratio to a threshold ratio value, and may determine that tested material 16 includes a crack or other defect in response to the difference being greater than the threshold ratio value.

In other examples in which electrical contacts 18 are positioned substantially symmetrically with respect to a symmetry of tested material 16, control module 12 may compare a first measured electrical parameter associated with a first extraction electrical contact and a second measured electrical parameter associated with a second extraction electrical contact that is symmetrical to the first extraction electrical contact with reference to a symmetry of tested material 16. In response to the first and second measured electrical signal parameters being substantially the same (e.g., within a threshold amount of each other) control module 12 may determine that tested material 16 does not include a crack or other defect. On the other hand, in response to the first and second measured electrical signal parameters not being substantially the same (e.g., different than each other by more than a threshold amount), control module 12 may determine that tested material 16 includes a crack or other defect. The threshold amount may be the same or slightly greater than the threshold amount used to determine the position of electrodes 18. For example, the threshold amount may be 1%, 5%, 10%, 20%, or the like. Control module 12 may compare the first and second measured electrical signal parameters by subtracting one of the first or second measured electrical signal parameters from the other of the first or second measured electrical signal parameters, by determining a ratio of one of the first or second measured electrical signal parameters to the other of the first or second measured electrical signal parameters, or the like, and then determining a percentage difference between the first or second measured electrical signal parameters.

Figure 2:
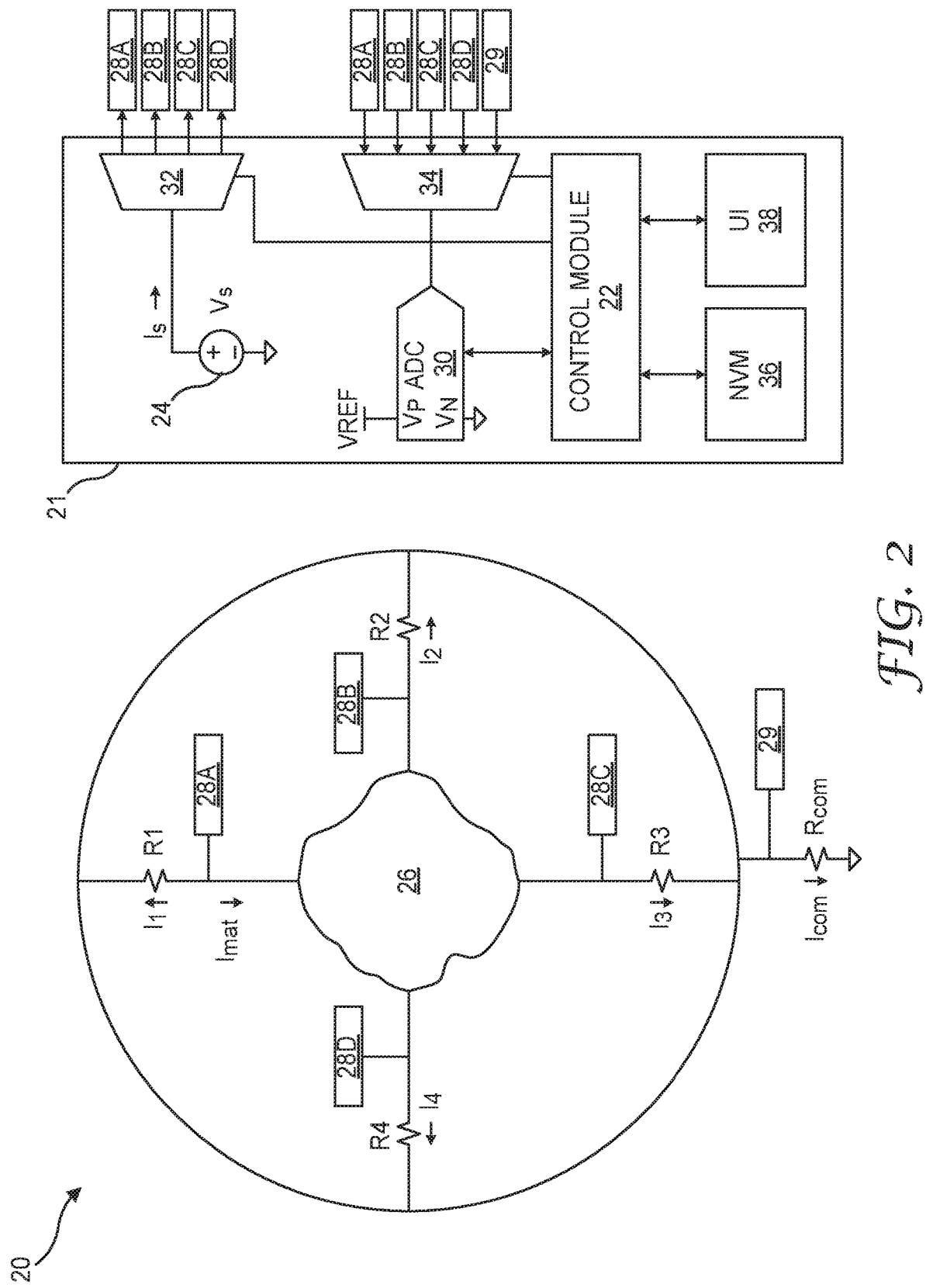

FIG. 2 is conceptual and schematic block diagram illustrating another example measurement system 20 for determining whether a tested material 26 includes a crack or other defect. Measurement system 20 includes tested material 26 and a measurement device 21. Measurement device 21 may include a control module 22, a voltage source 24, an analog-to-digital converter 30, an input switch array 32, an output switch array 34, a non-volatile memory (NVM) 36, and a user interface (UI) 38. Measurement system 20 also includes electrical contacts 28A-28D (collectively, "electrical contacts 28"), a common node 29, and resistors R1-R4 and $R_{com}$. Electrical contacts 28 may be attached to tested material 26, or may be separate from tested material 26 and brought into contact with tested material 26.

Figure 3:
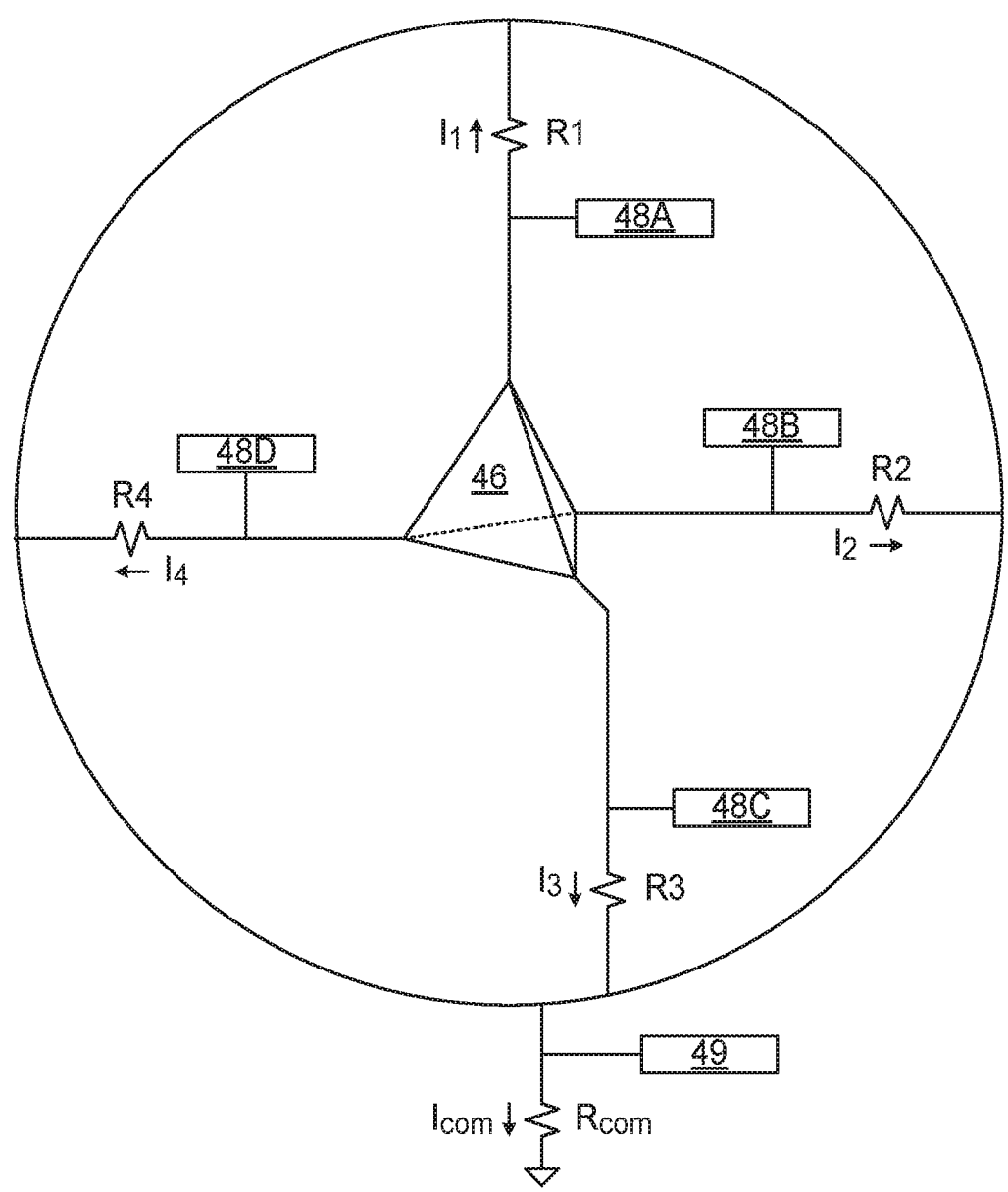
FIG. 3 is a conceptual diagram of an example tested material including three-dimensional symmetry and electrical contacts disposed symmetrically about the tested material.

Tested material 26 may be similar to or substantially the same as tested material 16 of FIG. 1. As shown in FIG. 2, in some examples, tested material 26 may be asymmetric. In other examples, as shown in FIG. 3, which is a conceptual diagram of an example tested material 46 including three-dimensional symmetry and electrical contacts 48A-48D disposed symmetrically about the tested material 46, tested material 46 may include a symmetry. In the example of FIG. 3, tested material 46 includes three-dimensional symmetry. FIG. 3 also illustrates a common node 49 and a common resistor, $R_{com}$.

Each of electrical contacts 28A-28D may be electrically coupled or connected to tested material 26. Common node 29 may be associated with a summing resistor, $R_{com}$, and may be used to measure a voltage associated with the summing resistor, $R_{com}$, for example a voltage drop across the summing resistor, $R_{com}$.

Each of electrical contacts 28 is associated with a respective resistor. First electrical contact 28A is associated with a first resistor, R1, second electrical contact 28B is associated with a second resistor, R2, third electrical contact 28C is associated with a third resistor, R3, fourth electrical contact 28D is associated with a fourth resistor, R4, and common node 29 is associated with summing resistor, $R_{com}$. Each of the resistors may have a known resistance, which may be the same or different than resistances of the other resistors. In some examples, each resistor is a precision resistor, meaning that each resistor has a tolerance of ±1% or less (e.g., an actual resistance value within 1% or less of its nominal resistance value). In some examples, each resistor may have a tolerance of ±0.5%, ±0.25%, ±0.10%, ±0.05%, or the like.

The summing resistor, $R_{com}$, is electrically coupled in series between outputs of the resistors R1-R4 and a terminal or return node of voltage source 24 (e.g., a ground terminal as shown in FIG. 2, or a positive terminal of voltage source 24 in other examples). For example, the summing resistor, $R_{com}$, may be electrically connected in series between common node 29 into which the outputs of the resistors R1-R4 connect and the terminal of voltage source 24. In this way, the summing resistor, $R_{com}$, allows measurement of all current passing through tested material 26. Electrical contacts 28, common node 29, and resistors R1-R4 and $R_{com}$ may be part of tested material 16 or measurement device 21.

Measurement device 21 also includes a voltage source 24. Voltage source 24 may be an example of electrical signal source 14 of FIG. 1, and may be configured to output a voltage signal, e.g., a DC voltage signal or an AC voltage signal, with selected characteristics (e.g., amplitude, frequency, phase, and the like). In examples in which the voltage signal is a DC voltage signal, the DC voltage signal may include a positive or negative signal, such that positive current flows from an input electrical contact selected from electrical contacts 28A-28D to extraction electrical contacts selected from electrical contacts 28A-28D or positive current flows from extraction electrical contacts selected from 28A-28D to an input electrical contact selected from electrical contacts 28A-28D (e.g., negative current flows from the input electrical contact to the extraction electrical contacts. In other words, although FIG. 2 illustrates the positive electrical contact of voltage source 24 being connected to input switch array 32 and the negative electrical contact of voltage source 24 being connected to ground/summing resistor, $R_{com}$, in other examples, the negative electrical contact of voltage source 24 may be connected to input switch array 32 and the positive electrical contact of voltage source 24 may be connected to ground/summing resistor, $R_{com}$. In some examples, voltage source 24 may include a power source, such as a battery, a capacitor, a supercapacitor, a transformer electrically connected to a mains voltage, or the like. In some examples, in addition to the power source, voltage source 24 may include analog or digital circuitry configured to receive the electrical signal from the power source and modify the electrical signal into a format suitable for output to components of measurement system 20. An output of voltage source 24 may be electrically connected to input switch array 32.

Measurement device 21 may include input switch array 32. Input switch array 32 includes at least one input and a plurality of outputs. The input may be electrically connected to an output (e.g., positive or negative terminal) of voltage source 24. Each respective output of input switch array 32 may be electrically connected to a respective electrical contact of electrical contacts 28. Additionally, input switch array 32 may be connected to control module 22, which may control positions of switches in input switch array 26. In some examples, input switch array 32 may include at least as many outputs as there are electrical contacts 28 coupled to test material 26. For example, in the example shown in FIG. 2, measurement system 20 includes four electrical contacts 28 coupled to test material 26, and input switch array 32 thus may include at least four outputs.

Control module 22 may control input switch array 32 to electrically connect a selected electrical contact of electrical contacts 28 to voltage source 24 as an input electrical contact. This allows voltage source 24 to output a voltage signal to the input electrical contact. In the example of FIG. 1, control module 22 has controlled input switch array 32 to electrically connect first electrical contact 28A to voltage source 24 as the input electrical contact.

Measurement device 21 also may include an output switch array 34. Output switch array 34 includes at least one output and a plurality of inputs. The output may be electrically connected to an input of ADC 30. Each respective input may be electrically connected to a respective electrical contact of electrical contacts 28 and to common node 29. Additionally, output switch array 34 may be connected to control module 22, which may control positions of switches in output switch array 34. In some examples, output switch array 34 may include at least one more input than there are electrical contacts 28 to account for common node 29. For example, in the example shown in FIG. 2, measurement system 20 includes four electrical contacts 28 and a common node 29, and output switch array 34 thus may include at least five inputs.

Control module 22 may control output switch array 34 to electrically connect a selected electrical contact of electrical contacts 28 or common node 29 to ADC 30 to measure a voltage using the selected electrical contact or common node 29. In some examples, control module 22 may control output switch array 34 to sequentially connect selected electrical contacts of electrical contacts 28 or common node 29 to ADC 30 to measure a respective voltage using the respective electrical contact or common node 29.

Measurement device 21 also may include ADC 30. ADC 30 may include at least a control input electrically connected to control module 22, which allows control module 22 to control operation of ADC 30 and read data from ADC 30, and at least one signal input electrically connected to output switch array 34. ADC 30 also may include reference voltage inputs. In some examples, a positive reference voltage input, VREF, may be connected between $V_P$ and $V_N$ (the ADC positive and negative reference voltage inputs, respectively). VREF may be derived from the power supply of measurement system 20, generated by a separate component (e.g. the Rcom resistor voltage drop), or be generated internally by ADC 30; the negative reference voltage input may be connected to ground. In other examples, the positive reference voltage input may be connected to an output of a first digital-to-analog converter (DAC) and the negative reference voltage input may be connected to an output of a second DAC (neither of which is shown in FIG. 2). Control module 20 may control the first and second DACs to output signals with selected voltages, which may affect the resolution of ADC 30.

In some examples, ADC 30 may be a differential ADC, which accepts two input signals and digitizes the voltage difference between the two input signals.

NVM device 36 may include any type of non-volatile memory. For example, NVM device 36 may include at least one of erasable programmable read-only memory (EPROM), electrically erasable programmable read-only memory (EEPROM), flash memory, magnetoresistive random access memory (MRAM), giant magnetoresistive random access memory (GMRAM), ferroelectric random access memory (FRAM), silicon-on-insulator metal-oxide-semiconductor (SOI MOS) memory, phase change random access memory (PRAM), chalcogenide random access memory (C-RAM), or carbon nanotube-based random access memory (NRAM).

NVM device 36 may be configured to store a set of control voltages associated with tested material 26. Control voltages are described above with respect to FIG. 1. In some examples, measurement device 21 may include NVM device 36. In other examples, NVM device 36 may be attached to tested material 26.

Measurement device 21 further includes a user interface (UI) device 38. UI device 38 may include an output device, an input device, or both. Input devices may include, for example, buttons, switches, a touchscreen, or the like. Output devices may include, for example, a light or light emitting diode (LED), a display, a speaker, a haptic device, or another device configured to output visible, audible, or perceivable information.

Measurement device 21 may include control module 22. Control module 22 may be similar to or substantially the same as control module 12 of FIG. 1, aside from the differences described herein. Control module 22 is configured to control operation of measurement system 20, including voltage source 24, ADC 30, input switch array 32, output switch array 34, NVM 36, and UI device 38. Control module 22 may include or be implemented in, for example, a processor. The processor may include one or more microprocessors, digital signal processors (DSP), application specific integrated circuits (ASIC), field programmable gate arrays (FPGA), or other digital logic circuitry. In some examples, a microprocessor may include at least one of voltage source 24, ADC 30, input switch array 32, output switch array 34, or NVM 36.

Control module 22 may be configured to control input switch array 32 to electrically connect a selected electrical contact of electrical contacts 28 to voltage source 24 to serve as an input electrical contact, such that voltage source 24 outputs a voltage signal to the input electrical contact.

The electrical contacts from electrical contacts 28 are electrically connected to common node 29. For example, as shown in FIG. 2, the outputs of each of resistors R1-R4 are electrically connected to common node 29. Each of the electrical contacts other than the selected input electrical contact serves as an extraction electrical contact.

Control module 22 may be configured to then cause voltage source 24 to output a voltage to the input electrical contact. The current generated by voltage source 24, $I_s$, flows out of voltage source 24, through input switch array 32, to the selected input electrical contact, first electrical contact 28A. At this point, the current splits into two currents, $I_1$ (series resistor R1 current) and $I_{mat}$ (the current into tested material 26). $I_{mat}$ flows into tested material 26 at the first electrical contact 28A and flows out of tested material 26 at the extraction electrical contacts (e.g., the non-driven electrical contacts; in this example, electrical contacts 28B, 28C, and 28D with currents $I_2$, $I_3$, and $I_4$). All electrical contact currents, $I_1$-$I_4$, are summed at the common node 29 and then returned to voltage source 24 via the ground node or negative terminal of voltage source 24.

While voltage source 24 is outputting the voltage signal to the input electrical contact, control module 22 may cause output switch array 34 to electrically connect a selected electrical contact of electrical contacts 28 or the common node 29 to ADC 30 to measure a voltage associated with the respective electrical contact. For example, control module 22 may cause output switch array 34 to sequentially electrically connect electrical contacts of the electrical contacts 28 and common node 29 to ADC 30 to measure the respective voltages.

Control module 22 then may determine respective currents based on the measured voltages and the resistance values of the resistors R1-R4 and $R_{com}$. Algebraically, for N electrical contacts, where contact q is the input electrical contact and contact p is one of the (N−1) current extraction electrical contacts (p≠q), and where R1-R4 are equal and have a value R:

$$I_q = (V_q - V_{com})/R = (V_s - V_{com})/R$$

$$I_p = (V_p - V_{com})/R$$

$$I_{com} = V_{com}/R_{com} = I_s$$

$$R_{com} = P^*R$$

$$I_{mat} = I_s - I_q =$$

$$I_{com} - I_q = (V_{com}/R_{com}) - (V_s - V_{com})/R = (([P+1]/P)^*V_{com} - V_s)/R$$

For a given input electrical contact, q, control module 22 may cause ADC 30 to measure the current of (N−1) extraction electrical contacts ($I_p$, q≠p).

In some examples, control module 22 may determine a respective ratio between each respective current associated with a respective extraction electrical contact and the current associated with a reference electrical contact, such as common node 29 (the common node voltage). By determining these ratios, control module 22 may reduce effects of conductivity changes in tested material 26 due to temperature changes, e.g., between a time at which control data is determined and a time at which measured data is determined. The ratio of a respective current, $I_p$, to the total material current, $I_{mat}$, yields the percentage of total material current at the respective extraction electrical contact p for an input electrical contact, q.

$$I_p/I_{mat} = [(V_p - V_{com})/R]/[(([P+1]/P)^*V_{com} - V_s)/R]$$

$$= (V_p - V_{com})/(([P+1]/P)^*V_{com} - V_s)$$

$$= ([V_p/V_{com}] - 1)/((([P+1]/P) - [V_s/V_{com}])$$

In some examples, control module 22 may calculate the respective currents and the total material current directly and then calculate the ratios.

In some examples, control module 22 may be configured to subsequently select another electrical contact of electrical contacts 28 as an input electrical contact and cause input switch array 32 to electrically connect the subsequently selected electrical contact to voltage source 24. Control module 22 may cause ADC 30 to perform the voltage measurements for the respective electrical contacts 28 and common node 29 and determine the currents or ratios as described above. Control module 22 may perform this selection and measurement technique for at least one input electrical contact, e.g., for each electrical contact of electrical contacts 28.

Control module 22 then may use the measured electrical signal parameters (e.g., voltages, currents, or ratios) to determine whether tested material 26 includes a crack or other defect. Control module 22 may implement any of the techniques described herein to determine whether tested material 26 includes a crack or other defect based on the measured electrical signal parameters.

In some examples, at least some of the components illustrated in FIG. 2 may be implemented in a microcontroller, which may reduce the number of individual components in a measurement device. FIG. 4 is a functional circuit diagram illustrating an example measurement system 50 for determining whether a tested material 56 includes a crack or other defect. Measurement system 50 of FIG. 4 includes an article 52 and a measurement device 54. Article 52 includes a tested material 56, a plurality of electrical contacts 58, only one of which is labeled in FIG. 4 for clarity. Aside from any differences described herein, each of these components may be similar to the corresponding components described with respect to FIGS. 1-3.

Article 52 also may include a substrate 60. Substrate 60 may include a flex circuit, a printed circuit board (PCB), or the like, to which electronic and electrical components may be mounted and electrically connected. For example, electrical contacts 58 may be mounted to substrate 60 and electrically connected to a contact signal bus 62. Substrate 60 may include an electrically insulating material that provides mechanical support for substrate 60 and a plurality of electrically conductive traces that electrically connect components mounted or connected to substrate 60. The electrically insulating material may include, for example, a polymer, ceramic, or other dielectric material. For instance, a flex circuit may include a flexible plastic, such as a polyimide, a polyester, a polyether ether ketone (PEEK), or the like. A PCB may include, for example, a glass epoxy, a phenolic material, a polyimide, a polyester, or the like. In some examples, the PCB may include a reinforcement material, such as paper, fiberglass, or the like, impregnated or coated with a glass epoxy, a phenolic material, a polyimide, a polyester, or the like. The conductive traces in the PCB or flex circuit may include, for example, copper, silver, aluminum, or the like.

Measurement device 54 includes a micro controller 68, a user interface device 70, a voltage source 64, resistors R1-RM. Microcontroller 68 includes a control module 72, an ADC 74, a multiplexer 76, an NVM device 78, an N-bit output register 80, an N-bit tristate register 82, a plurality of tristate switches 84A-84M (collectively, "tristate switches 84"), and a plurality of ports 86A-86N (collectively, "ports 86"). Aside from any differences described herein, each of these components may be similar to the corresponding component (if any) described with respect to FIGS. 1-3. Although not shown in FIG. 4, in some examples, measurement device 54 and article 52 may be electrically connected using optional electrical connectors.

In measurement device 54, the input switch array and output switch array are implemented in multiplexer 76, N-bit output register 80, N-bit tristate register 82, and tristate switches 84. Microcontroller 68 controls operation of measurement system 50. For example, control module 72 may control N-bit output register 80 and N-bit tristate register 82 to control positions of tristate switches 84 to connect a selected one of electrical contacts 58 to VDD from voltage source 64, to place the remaining electrical contacts of electrical contacts 58 in a high impedance (open) state as extraction electrodes, and connect a selected node (e.g., one of electrical contacts 58, one of ports 86A-86N, or the like) to multiplexer 76. Control module 72 also controls multiplexer 76 to select a line to be input to ADC 74.

For example, to select an electrical contact of electrical contacts 58 as an input electrical contact, control module 72 causes the appropriate buffer to be enabled and set high, which switches its output to VDD of voltage source 64. Control module 72 causes all other output buffers to be disabled (Tristated), which puts the output in a high impedance state. Control module 72 then causes N electrical contacts 58 and the common node 86N to be scanned sequentially by multiplexor 76; when selected, the input is applied to ADC 74 and its value is digitized and stored in NVM device 78. When the scan is completed, control module 72 may cause another electrical contact to be selected as the input electrical contact and the scanning process to be repeated. Control module 72 may repeat the select and scan loop until all electrical contacts 58 have been input electrical contacts.

When the select and scan loop is completed, control module 72 may compare the resulting data to control data stored in NVM 78, as described above with respect to FIG. 1, or may implement another technique for determine whether tested material 56 includes a crack or other defect, as described herein. Based on the outcome, control module 72 may write the appropriate output to the UI 70 to indicate the appropriate state (e.g., fault-free or fault detected).

In this way, the combination of N-bit output register 80, N-bit tristate register 82, tristate switches 84, and multiplexer 76 implement similar functionality as input switch array 32 and output switch array 34 of FIG. 2.

Figure 4:
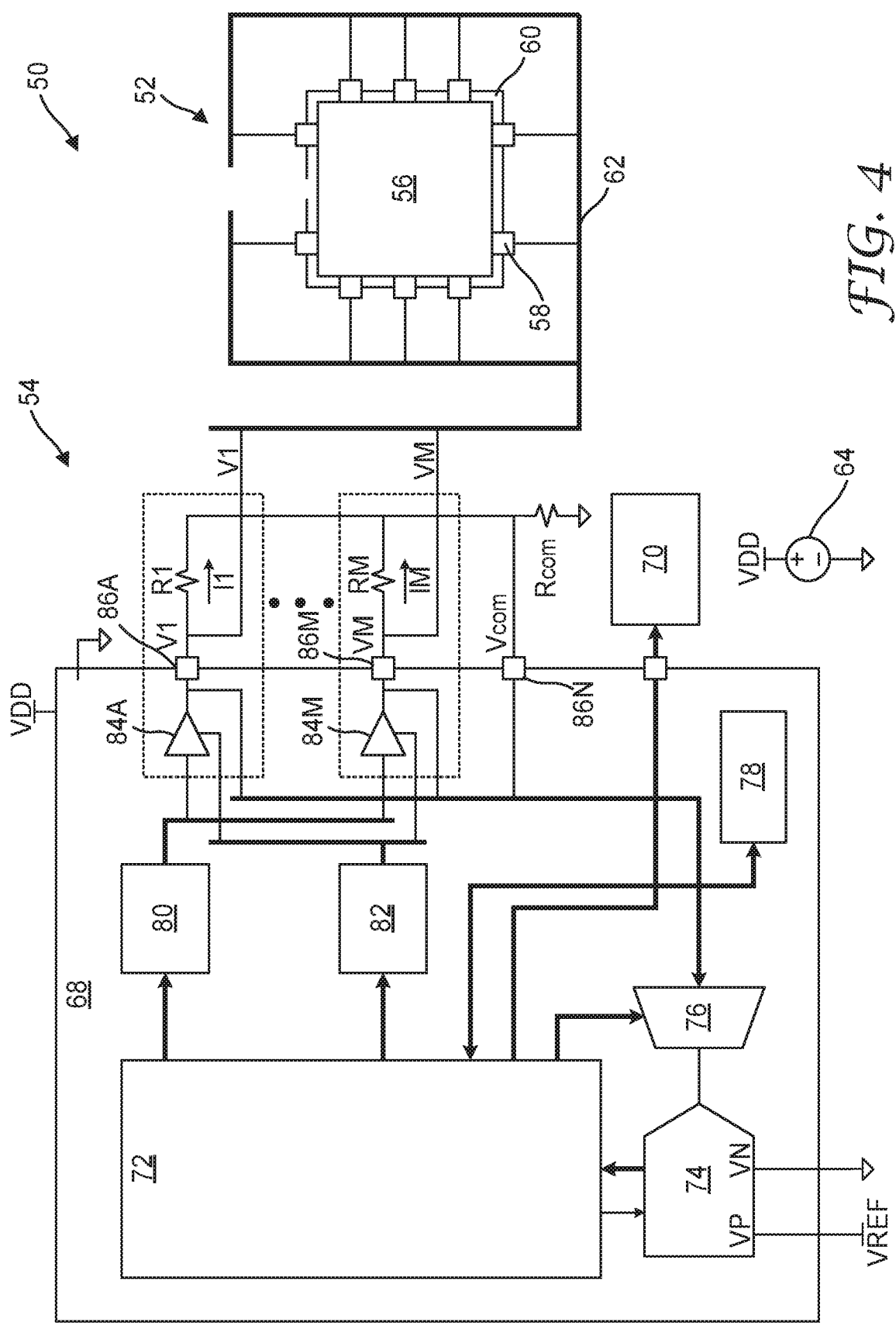
FIGS. 4 and 5 are functional circuit diagrams illustrating example measurement systems for determining whether a tested material includes a crack or other defect.
Figure 5:
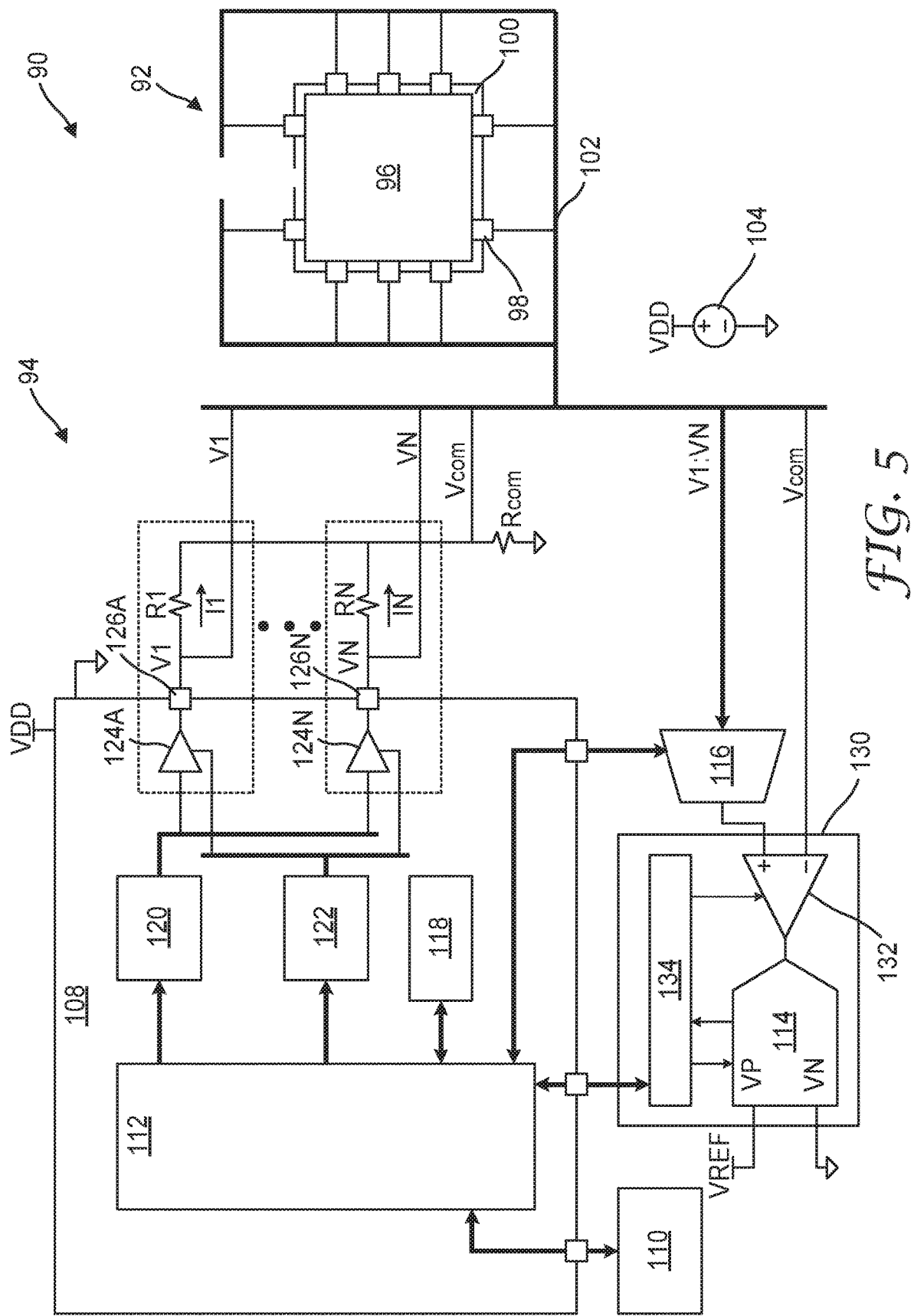

In some examples, if higher resolution measurements are desired, the system in FIG. 5 may be used to make a fault determination. FIG. 5 is a functional circuit diagram illustrating an example measurement system 90 for determining whether a tested material 96 includes a crack or other defect. The basic elements and architecture in FIG. 5 may be the same as those in FIG. 4, aside from the differences described herein. For example, measurement system 90 includes an article 92, which includes tested material 96, a substrate 100, a contact signal bus 102, and a plurality of electrical contacts 98. Measurement system 90 also includes a measurement device 94, which includes a microcontroller 108. Microcontroller 108 includes a control module 112, an NVM device 118, an N-bit output register 120, an N-bit tristate register 122, tristate switches 124A-124N, and ports 126A-126N. Measurement device 94 also includes a user interface 110 and a voltage source 104.

Unlike measurement system 50 of FIG. 4, in measurement system 90 of FIG. 5, ADC 114 and output multiplexer 116 are separate from microcontroller 108; ADC 114 as part of ADC module 130 and output multiplexer 116 as a separate device. Control module 112 performs the control functions for measurement device 94. Output multiplexor 116 and ADC module 130 are controlled by control module 112 via separate input/output ports of microcontroller 108. In some examples, ADC 114 may provide higher resolution than an ADC internal to a microcontroller. Further, in some examples, ADC module 130 may include an internal difference amplifier 132, which may have programmable gain.

Since the material currents are equal to the difference between the contact voltage (e.g., V1) and the common voltage (e.g., Vcom), difference amplifier 132 is connected such that the positive input receives the contact voltages via multiplexer 116 and the negative input receives the common voltage, Vcom. In this way, ADC 114 may digitize the difference between the contact voltage and the common voltage directly. Since the current equals the voltage difference divided by the resistance associated with the respective electrical contact (e.g., R1-RN), in examples in which R1-RN are the same or substantially similar, determining a ratio between voltages associated with two electrical contacts does not require a division by the resistance.

The programmable gain feature of difference amplifier 132 allows the voltage differences, which may be quite small, to be amplified before digitization which improves the dynamic range and resolution of the measurements. If a single-ended ADC is used, then multiplexer 116 may be an (N+1):1 switch with the addition of an input for the Vcom signal.

Figure 6:
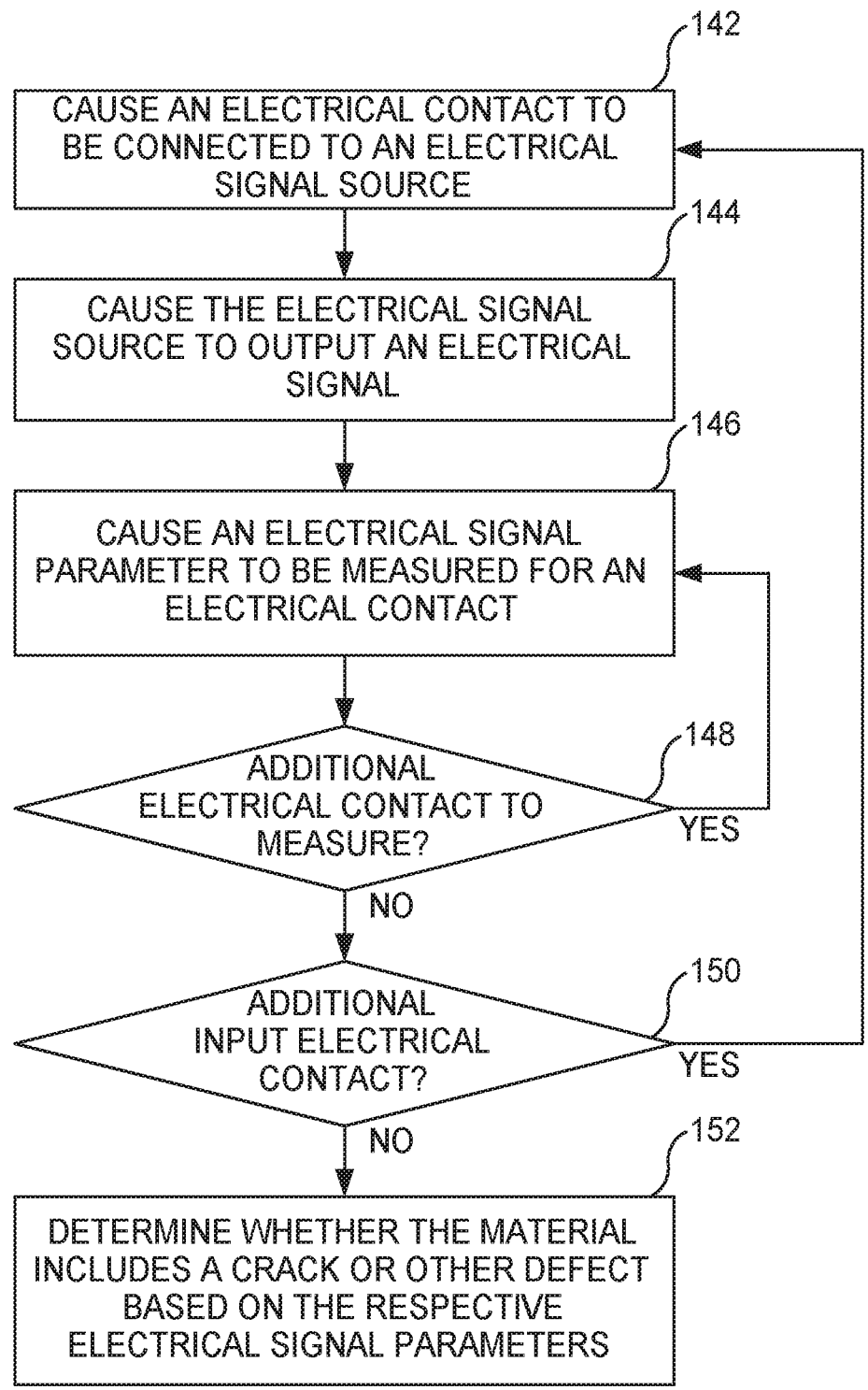
FIG. 6 is a flow diagram illustrating an example technique for determining whether a tested material includes a crack or other defect based on measured electrical signal parameters.

FIG. 6 is a flow diagram illustrating an example technique for determining whether a tested material includes a crack or other defect. The technique of FIG. 6 will be described with concurrent reference to measurement system 20 of FIG. 2, but it will be understood that other systems may perform the technique of FIG. 6 (e.g., system 10 of FIG. 1, system 50 of FIG. 4, or system 90 of FIG. 5), and that measurement system 20 may be used to perform other techniques.

The technique of FIG. 6 may include causing, by control module 22, an electrical contact of electrical contacts 28 to be electrically connected to an electrical signal source, e.g., voltage source 24, as an input electrical contact (142). For example, control module 22 may control input switch array 32 to electrically connect a selected one of electrical contacts 28 to voltage source 24. In other examples, a control module 72 may control an N-bit output register 80, an N-bit tristate register 82, a plurality of tristate switches 84 (FIG. 4) to electrically connect a selected electrical contact to a voltage source 64. All electrical contacts of electrical contacts 28 are also electrically connected to common node 29.

The technique of FIG. 6 also includes causing, by control module 22, an electrical signal source, such as voltage source 24, to output an electrical signal to the selected input electrical contact (144). The voltage source may output the voltage signal with selected parameters, including, for example, DC or AC of a predetermined frequency, a selected voltage, a selected duration, a selected polarity or sign, and the like. In some examples, the type of electrical signal may depend on the composition of tested material 86. For example, a DC signal may be used to measure a voltage of an electrically conductive or electrically semiconductive material, while an AC signal may be used to measure a voltage of an electrically conductive material, an electrically semiconductive material, or a dielectric material.

The technique of FIG. 6 also includes, while voltage source 24 is outputting the voltage signal to the input electrical contact (144), causing, by control module 22, ADC 30 to measure an electrical signal parameter associated with a respective resistor associated with an electrical contact (146). The electrical contact may include any of electrical contacts 28 and common node 29 including (optionally) the electrical contact selected as the input electrical contact. For example, control module 22 may control output switch module 34 to electrically connect a selected electrical contact of electrical contacts 28 or common node 29 to an input of ADC 30. ADC 30 may digitize the voltage and, in some examples, store the digitized voltage using NVM 36, e.g., in a table in which the digitized voltage is associated with the input electrical contact and extraction electrical contact.

In some examples, the ADC may directly determine a ratio, e.g., between the measured voltage and the common or summed voltage, as described with reference to FIG. 5. If the positive reference, Vp, of ADC 114 is connected to the common node voltage Vcom, and the common node summing resistance, Rcom, is a multiple, P, of the contact resistor value, then the ADC conversion code (for an M bit ADC) will be: $ADC(V_N)=(2^{M}-1)*V_N/Vcom=(2^{M}-1)*I_N*R/I_{total}*P*R=(2^{M}-1)*I_N/I_{total}*P$ The technique of FIG. 6 may further include determining, by control module 22, whether there is an additional electrical contact for which to measure an electrical signal parameter (148). In response to determining that there is an additional electrical contact for which to measure an electrical signal parameter (the "YES" branch of decision block 148), control module 22 may cause ADC 30 to measure an electrical signal parameter associated with the respective resistor associated with the additional electrical contact or common node 29 (146). Control module 22 may repeat this determining (148) and measuring (146) technique until control module 22 determines that there are not additional electrical contacts or common node 29 for which to measure an electrical signal parameter (the "NO" branch of decision block 148).

In some examples, control module 22 optionally then may determine whether an additional electrical contact of electrical contacts 28 is to be electrically connected to voltage source 24 as an input electrical contact (150). For example, in some implementations, control module 22 may be configured to utilize each electrical contact of electrical contacts 28 as an input electrical contact. Control module 22 may determine whether any electrical contact from electrical contacts 28 has not been used as an input electrical contact. In response to determining that an electrical contact of electrical contacts 28 has not been used as an input electrical contact (the "YES" branch of decision block 150), control module 22 may cause input switch array 32 to electrically connect the electrical contact to voltage source 24 (142). The remaining electrical contacts function as extraction electrical contacts. Control module 22 then may cause the electrical signal source (e.g., voltage source 24) to output an electrical signal to the selected input electrical contact (144) and cause ADC to measure an electrical signal parameter for each electrical contact of electrical contacts 28 and, optionally, common node 29 (146 and 148). Control module 22 may be configured to repeat this technique for each input electrical contact, until control module 22 determines that no additional electrical contacts of electrical contacts 28 are to be used as an input electrical contact (the "NO" branch of decision block 150).

Figure 7:
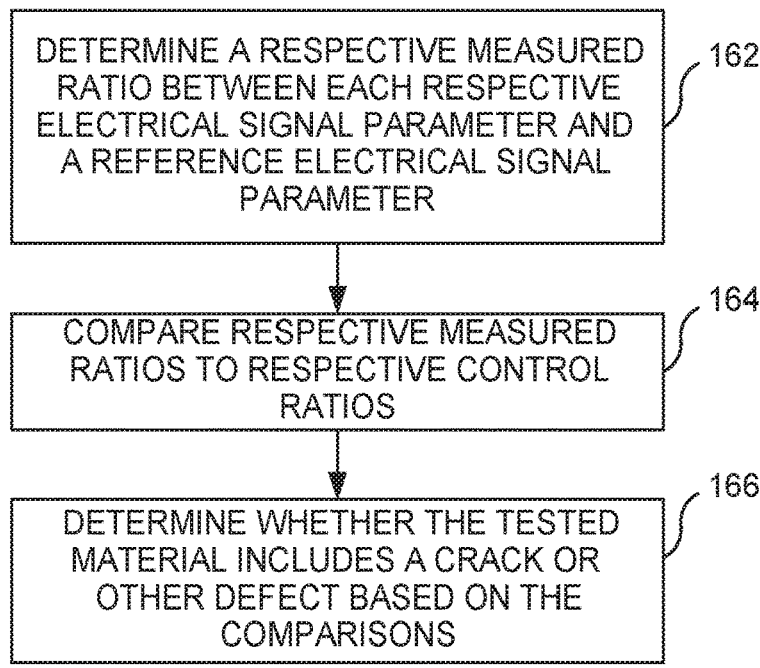
FIG. 7 is a flow diagram illustrating another example technique for determining whether a tested material includes a crack or other defect based on measured electrical signal parameters.
Figure 8:
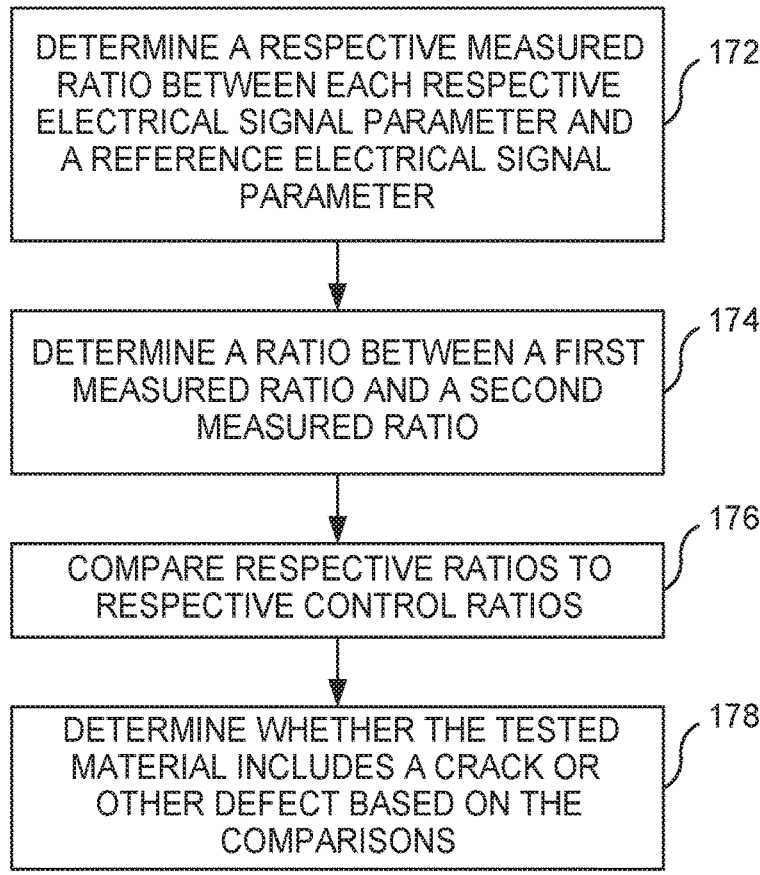
FIG. 8 is a flow diagram illustrating another example technique for determining whether a tested material includes a crack or other defect based on measured electrical signal parameters.

Control module 22 then may determine whether tested material 26 includes a crack or other defect based on the electrical signal parameters (152). Control module 22 may utilize any one or more of a variety of techniques to determine whether tested material 26 includes a crack or other defect based on the electrical signal parameters (152). Two examples are illustrated in FIGS. 7 and 8. FIG. 7 is a flow diagram illustrating another example technique for determining whether tested material 26 includes a crack or other defect based on measured electrical signal parameters. The technique of FIG. 7 includes determining, by control module 22 or ADC 30, a respective measured electrical signal parameter ratio between each respective electrical signal parameter (e.g., voltage or current) associated with a respective extraction electrical contact of electrical contacts 28 and a reference electrical signal parameter (e.g., voltage or current) associated with common node 29 (162). In some examples, as described above, ADC 30 or other measurement circuitry may be configured to measure a voltage associated with each electrical contact of electrical contacts 28 and common node 29 while voltage source 24 is outputting an electrical signal to the input electrical contact.

Control module 22 may be configured to receive these voltages from ADC 30 or retrieve the voltages from a memory, such as NVM 36. Control module 22 then may determine the respective measured ratios. For example, in implementations in which R1-R4 and $R_{com}$ each have substantially the same resistance value, control module 22 may determine the respective measured ratios using the measured voltages. As another example, in implementations in which one or more of R1-R4 and $R_{com}$ is a different resistance than at least one other of R1-R4 and $R_{com}$, control module 22 may first determine respective current values based on the respective measured voltages and the respective resistor values, then may determine respective measured ratios of currents associated with respective electrical contacts 28 and the common current associated with common node 29. In other examples, ADC 30 may include a differential ADC or the measurement system may include a differential amplifier whose output is input into the ADC, and the ADC may directly determine the respective measured ratios, as described above with respect to FIG. 5.

The technique of FIG. 7 may also include comparing, by control module 22, respective measured ratios to respective control ratios (164). The control ratios may be based on tested material 26, a model, or an average of a plurality of tested materials that are similar to or substantially the same as tested material 26. For example, control module 22 or another similar control module may determine the control ratios at a time at which tested material 26 is manufactured, or a time at which an independent measurement (e.g., X-ray radiology or X-ray CT scan) may be used to verify that tested material 26 is intact, undamaged, or does not include a crack. Control module 22 or the other similar control module may determine by control ratios by performing steps (142)-(150) of FIG. 6 and step (162) of FIG. 7.

In other examples, the control electrical signal parameters may be determined using a model of the tested material in an intact (undamaged) state. For example, control module 22 may execute the model of tested material 26 and determine the control ratios based on the model. In some examples, the model may include a physics-based model of the electrical properties of tested material 26, such as the physics-based model described below. In some other examples, the control ratios may be determined as an average (e.g., mean) of a plurality of similar materials (e.g., in geometry and composition) that are known to be intact (undamaged). These control ratios may be stored (e.g., in NVM 36) for later use.

Each respective measured ratio and respective control ratio may be associated with a respective input electrical contact and a respective extraction electrical contact. As such, control module 22 may compare a respective measured ratio with a corresponding (associated with the same input electrical contact and extraction electrical contact) control ratio. For example, for each comparison, control module 22 may determine whether the measured ratio is the same as the control ratio within a predetermined threshold amount. The comparison may be a ratio or a difference. The predetermined threshold amount may be a percentage of the control ratio, e.g., 10% of the control ratio, 5% of the control ratio, 2% of the control ratio, 1% of the control ratio or the like.

Control module 22 then may determine whether tested material 26 includes a crack or other defect based on the comparisons (166). For example, control module 22 may be configured to determine that the tested material 26 includes a crack or other defect if any of the comparisons exhibits a difference greater than the predetermined threshold amount. As another example, control module 22 may be configured to determine that the tested material 26 includes a crack or other defect if more than a threshold number of comparisons exhibit a difference greater than the predetermined threshold amount.

FIG. 8 is a flow diagram illustrating another example technique for determining whether tested material 26 includes a crack or other defect based on measured electrical signal parameters. Like the technique of FIG. 7, the technique of FIG. 8 includes determining, by control module 22 or ADC 30, a respective measured electrical signal parameter ratio between each respective electrical signal parameter (e.g., voltage or current) associated with a respective extraction electrical contact of electrical contacts 28 and a reference electrical signal parameter (e.g., voltage or current) associated with common node 29 (172). In some examples, as described above, ADC 30 or other measurement circuitry may be configured to measure a voltage associated with each electrical contact of electrical contacts 28 and common node 29 while voltage source 24 is outputting an electrical signal to the input electrical contact.

Control module 22 may be configured to receive these voltages from ADC 30 or retrieve the voltages from a memory, such as NVM 36. Control module 22 then may determine the respective measured ratios. For example, in implementations in which R1-R4 and $R_{com}$ each have substantially the same resistance value, control module 22 may determine the respective measured ratios using the measured voltages. As another example, in implementations in which one or more of R1-R4 and $R_{com}$ is a different resistance than at least one other of R1-R4 and $R_{com}$, control module 22 may first determine respective current values based on the respective measured voltages and the respective resistor values, then may determine respective measured ratios of currents associated with respective electrical contacts 28 and the common current associated with common node 29. In other examples, ADC 30 may include a differential ADC or the measurement system may include a differential amplifier whose output is the input into the ADC, and the ADC may directly determine the respective measured ratios, as described above with respect to FIG. 5.

The technique of FIG. 8 may also include determining, by control module 22, a ratio between a first measured ratio and a second measured ratio (174). The first measured ratio may be associated with a first extraction electrical contact, and the second measured ratio may be associated with a second extraction electrical contact. In some examples, control module 22 may determine a respective ratio for each unique combination of measured ratios.

The technique of FIG. 8 also includes comparing, by control module 22, respective ratios (of a first measured ratio to a second measured ratio) to respective control ratios (178). The control ratios may be based on tested material 26, a model, or an average of a plurality of tested materials that are similar to or substantially the same as tested material 26. For example, control module 22 or another similar control module may determine the control ratios at a time at which tested material 26 is manufactured, or a time at which an independent measurement (e.g., X-ray radiology or X-ray CT scan) may be used to verify that tested material 26 is intact, undamaged, or does not include a crack. Control module 22 or the other similar control module may determine the control ratios by performing steps (142)-(150) of FIG. 6 and steps (172) and (174) of FIG. 8.

In other examples, the control electrical signal parameters may be determined using a model of the tested material in an intact (undamaged) state. For example, control module 22 may execute the model of tested material 26 and determine the control ratios based on the model. In some examples, the model may include a physics-based model of the electrical properties of tested material 26, such as the physics-based model described below. In some other examples, the control ratios may be determined as an average (e.g., mean) of a plurality of similar materials (e.g., in geometry and composition) that are known to be intact (undamaged). These control ratios may be stored (e.g., in NVM 36) for later use.

Each respective ratio and respective control ratio may be associated with a respective input electrical contact and a respective pair of extraction electrical contacts. As such, control module 22 may compare a respective ratio with a corresponding (associated with the same input electrical contact and pair of extraction electrical contacts) control ratio. For example, for each comparison, control module 22 may determine whether the ratio is the same as the control ratio within a predetermined threshold amount. The comparison may be a ratio or a difference. The predetermined threshold amount may be a percentage of the control ratio, e.g., 10% of the control ratio, 5% of the control ratio, 2% of the control ratio, 1% of the control ratio or the like.

Control module 22 then may determine whether tested material 26 includes a crack or other defect based on the comparisons (178). For example, control module 22 may be configured to determine that the tested material 26 includes a crack or other defect if any of the comparisons exhibits a difference greater than the predetermined threshold amount. As another example, control module 22 may be configured to determine that the tested material 26 includes a crack or other defect if more than a threshold number of comparisons exhibit a difference greater than the predetermined threshold amount.

As a further example, control module 22 may determine whether tested material 26 includes a crack or other defect by determining an overall score for tested material 26. For example, control module 22 may sum all measured ratios associated with a respective extraction electrical contact (e.g., for multiple input electrical contacts) to generate a single value associated with each respective extraction electrical contact. Control module 22 then may mathematically manipulate these values to arrive at a single score for tested material 26. For example, control module 22 may sum the measured ratios, take each measured ratio to a predetermined power and sum the products, average the measured ratios, determine a weighted average of the measured ratios, or the like to determine a single score for tested material 26. Control module 22 then may compare the single score to a threshold score value and determine that tested material 26 includes a crack or other defect if the single score is greater than the threshold score value.

As another example, in implementations in which electrical contacts 28A-28D are positioned symmetrically about tested material 26 with reference to a symmetry of tested material 26, an input electrical contact may be positioned on the symmetry of tested material 26, e.g., on a plane of symmetry of tested material 26. A first extraction electrical contact and a second extraction electrical contact may be positioned symmetrically with reference to the symmetry of tested material 26, e.g., with reference to a plane of symmetry of tested material 26. In such an example, a first measured electrical signal parameter or measured ratio associated with the first extraction electrical contact and a second measured electrical signal parameter or measured ratio associated with the second extraction electrical contact are expected to be substantially the same (e.g., the same or nearly the same) in the absence of a crack or other defect in tested material 26, assuming a homogeneous material. For example, in the absence of a crack or defect in tested material 26, the first measured electrical signal parameter or measured ratio and the second measured electrical signal parameter or measured ratio may be within a predetermined percentage of each other, such as, for example, within about 20%, 10%, 5%, or 1% of each other. Any difference between the first and second measured electrical signal parameter or measured ratio that is greater than a threshold difference may indicate that tested material 26 includes a crack or other defect. The difference may be determined by subtracting the first measured electrical signal parameter or measured ratio from the second measured electrical signal parameter or measured ratio (or vice versa) or by determining a ratio between the first measured electrical signal parameter or measured ratio and the second measured electrical signal parameter or measured ratio (or vice versa).

As a further example, electrical contacts 28A-28D may be positioned so that, for each group that includes an input electrical contact and an extraction electrical contact, the measured electrical signal parameter or measured ratio in the absence of a crack or other defect is substantially the same. The respective groups of electrical contacts may or may not be symmetric to another group of electrical contacts, and tested material 26 may or may not include a symmetry. As such, regardless of the groups of electrical contacts selected as the first group of electrical contacts and the second group of electrical contacts, in the absence of a crack or other defect in material 26, the first measured electrical signal parameter or measured ratio and the second measured electrical signal parameter or measured ratio may be substantially the same (e.g., the same or nearly the same). Any difference between measured electrical signal parameter or measured ratios that is greater than a threshold difference may indicate that tested material 26 includes a crack or other defect. The difference may be determined by subtracting the first measured electrical signal parameter or measured ratio from the second measured electrical signal parameter or measured ratio (or vice versa) or by determining a ratio between the first measured electrical signal parameter or measured ratio and the second measured electrical signal parameter or measured ratio (or vice versa).

As an additional example, control module 22 may calculate an approximate impedance distribution within tested material 26 to determine whether tested material 26 includes a crack or other defect (152). In some examples, reconstruction of the impedance distribution may be achieved by minimizing the difference between the output of a physics-based simulation tool with respective control voltages, and the respective measured voltages. For example, control module 22 may be programmed with a finite element model (FEM) of tested material 26 which implements the physics-based simulation. The FEM of tested material 26 may include substantially accurate (e.g., accurate or approximately accurate) geometry of tested material 26 (e.g., the shape and volume of tested material 26), and also may include substantially accurate (e.g., accurate or approximately accurate) locations of electrical contacts 28 attached to tested material 26. In some examples, the FEM of tested material 26 may additionally include representative properties of tested material 26, including, for example, conductivity, resistivity, other related electrical properties, and the like. The FEM of tested material 26 may include representative properties of tested material 26 for each respective node representing tested material 26.

Calculating the approximate impedance distribution to determine whether tested material 26 includes a crack or other defect is an ill-posed inverse problem, in which the outputs (the respective measured electrical signal parameters or measured ratios) are known but the properties of tested material 26 that produce the outputs are unknown. Moreover, more than one set of properties of tested material 26 may produce the outputs. Hence, control module 22 may utilize a regularization technique to constrain the solution to solutions more likely to represent the properties of tested material 26 that would produce the respective measured electrical signal parameters or measured ratios.

In particular, control module 22 may generate an objective function which combines outputs of the physics-based model, respective control electrical signal parameters or control ratios, the respective measured electrical signal parameters or measured ratios, and the regularization term. For example:

$$\underset{x}{\mathrm{argmin}}\left\{F(x) := \frac{1}{2}\|f(x)-y\|_{\ell_2}^2 + \lambda\frac{1}{2}\|Rx\|_{\ell_2}^2\right\}$$

where x is the approximate change in impedance distribution, f is an operator calculating the simulated difference in equivalent impedances based on input x utilizing the physics-based simulation, y is the measured difference in measured electrical signal parameters or measured ratios, $l_2$ is a chosen norm, R is the regularization matrix, and λ is the chosen weight of the regularization or regularization parameter. Control module 22 may determine respective model control measured electrical signal parameters or measured ratios based on the physics-based model and inputs representative of the electrical signal(s) applied to the respective input electrical contacts. The respective model control measured electrical signal parameters or measured ratios may be associated with respective extraction electrical contacts for each input electrical contact used to collect the control electrical signal parameters or control ratios from tested material 26. Control module 22 then may determine, using the physics-based model and inputs representative of the electrical signal(s) applied to the respective pairs of drive electrical contacts, respective model measured electrical signal parameters or measured ratios. The respective model measured electrical signal parameters or measured ratios may be associated with respective extraction electrical contacts for each respective input electrical contact used to collect the measured electrical signal parameters or measured ratios from tested material 26. For each respective model measured electrical signal parameter or measured ratio, control module 22 may determine a respective difference between the respective model measured electrical signal parameter or measured ratio and the respective model control electrical signal parameter or control ratio (f(x) in the equation above).

Control module 22 also may determine a respective difference between the respective measured electrical signal parameters or measured ratios and the respective control electrical signal parameters or control ratios for each respective measured electrical signal parameters or measured ratios measured using tested material 26 to generate a set of actual measured electrical signal parameter or measured ratio differences (y in the equation above).

Control module 22 then may minimize the objective function by updating one or more parameters of the physics-based model. Control module 22 may continue to iterate the model until a stopping criterion is reached. Control module 22 then may determine the approximate impedance distribution (or approximate change in impedance distribution) that is representative of the condition of tested material 26. When iteration completes the input to the model is the approximate impedance distribution.

Control module 22 may then determine whether tested material 26 includes a crack or other defect based on the approximate change in impedance distribution. For example, control module 22 may determine whether tested material 26 includes a crack or other defect based on the magnitude and location of the approximate impedance change within the material. In some examples, only the real portion of the impedance—the conductivity or resistivity—may be used by control module 22 to determine whether tested material 26 includes a crack or other defect.

In some examples, rather than utilizing respective control electrical signal parameters or control ratios and respective model control electrical signal parameters or control ratios, control module 22 may determine an approximate impedance distribution using an absolute form of the objective function, in which x is the impedance distribution, f is an operator calculating a set of the simulated equivalent impedances based on input x utilizing the physics-based simulation, y is a set of the measured electrical signal parameters or measured ratios, $l_2$ is a chosen norm, R is the regularization matrix, and λ is the chosen weight of the regularization or regularization parameter.

In any of the techniques described herein, control module 22 may output an indication of the determination of whether tested material 26 includes a crack or other defect to UI device 38 for output to a user. In some examples, the representation may include a simplified output, such as an indication of "Yes" or "No," "Crack" or "No Crack," "Damaged" or "Intact," or the like. The representation may be textual, icon-based, color-based, audible, haptic, or the like. For example, the representation may include a green light to represent that tested material 26 is still intact or a red light to represent that tested material 166 is damaged or includes a crack or other defect.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), ferroelectric RAM (FRAM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Clause 1: A measurement system including an electrical signal source; a plurality of electrical contacts electrically coupled to a tested material; a respective resistor associated with each electrical contact; a common node to which the respective resistors are electrically connected; and a control module. The control module may be configured to: cause the electrical signal source to be electrically connected to a selected electrical contact of the plurality of electrical contacts as an input electrical contact, wherein the remaining electrical contacts of the plurality of electrical contacts are electrically connected to a return node of the electrical signal source as extraction electrical contacts; cause the electrical signal source to output an electrical signal to the input electrical contact; cause a respective electrical signal parameter to be determined at the respective resistor associated with each respective extraction electrical contact; and determine whether the tested material includes a crack or other defect based on the respective electrical signal parameters.

Clause 2: The measurement system of clause 1, further comprising a summing resistor electrically connected between the common node and the return node, wherein the control module is further configured to: cause a reference electrical signal parameter to be determined at the common node; determine a respective electrical signal parameter ratio between each respective electrical signal parameter and the reference electrical signal parameter; and determine whether the tested material includes a crack or other defect based on the respective electrical signal parameter ratios.

Clause 3: The measurement system of clause 2, wherein the control module is configured to determine whether the tested material includes a crack or other defect based on the respective electrical signal parameter ratios by at least: comparing at least one of the respective electrical signal parameter ratios to a corresponding control electrical signal parameter ratio, wherein the control electrical signal parameter ratio is associated with the same input electrical contact and the same extraction electrical contact.

Clause 4: The measurement system of clause 2, wherein the control module is configured to determine whether the tested material includes a crack or other defect based on the respective electrical signal parameter ratios by at least: determining a first ratio between a first electrical signal parameter ratio and a second electrical signal parameter ratio; and comparing the first ratio to a control ratio, wherein the control ratio is associated with the same input electrical contact and the same extraction electrical contacts with which the first electrical signal parameter and the second electrical signal parameter are associated.

Clause 5: The measurement system of clause 1, wherein the control module is configured to determine whether the tested material includes a crack or other defect based on the respective electrical signal parameters by at least: comparing at least one of the respective electrical signal parameters to a corresponding control electrical signal parameter, wherein the control electrical signal parameter is associated with the same input electrical contact and the same extraction electrical contact.

Clause 6: The measurement system of clause 1, wherein the control module is configured to determine whether the tested material includes a crack or other defect based on the respective electrical signal parameters by at least: determining a first ratio between a first electrical signal parameter and a second electrical signal parameter; and comparing the first ratio to a control ratio, wherein the control ratio is associated with the same input electrical contact and the same extraction electrical contacts with which the first electrical signal parameter and the second electrical signal parameter are associated.

Clause 7: The measurement system of clause 1, wherein the control module is configured to determine whether the tested material includes a crack or other defect based on the respective electrical signal parameters by at least: calculating an approximate change in impedance distribution within the tested material based on a physics-based simulation, inputs representative of the electrical signal output by the electrical signal source to the input electrical contact, the respective electrical signal parameters, and respective control electrical signal parameters; and determining whether the material includes the crack or other defect based on the change in impedance distribution.

Clause 8. The measurement system of clause 7, wherein calculating the approximate change in impedance distribution within the tested material comprises minimizing an output of an objective function:

$$\operatorname*{argmin}_{x}\left\{F(x) := \frac{1}{2}\|f(x) - y\|_{\ell_2}^2 + \lambda \frac{1}{2}\|Rx\|_{\ell_2}^2\right\},$$

wherein x is the approximate change in impedance distribution, f is an operator calculating a set of simulated difference in electrical signal parameters based on input x utilizing the physics-based simulation, y is a set of differences between the respective electrical signal parameters and the respective control electrical signal parameters, $l_2$ is a chosen norm, R is a regularization matrix, and $\lambda$ is a chosen weight of the regularization or a regularization parameter.

Clause 9: The measurement system of clause 1, wherein the computing device is configured to determine whether the tested material includes a crack or other defect based on the respective electrical signal parameters by at least: calculating an approximate impedance distribution within the tested material based on a physics-based simulation, inputs representative of the electrical signal output by the electrical signal source to the input electrical contact, and the respective electrical signal parameters; and determining whether the material includes the crack or other defect based on the approximate impedance distribution.

Clause 10: The system of clause 9, wherein calculating the approximate impedance distribution within the material comprises minimizing an output of an objective function:

$$\operatorname*{argmin}_{x}\left\{F(x) := \frac{1}{2}\|f(x) - y\|_{\ell_2}^2 + \lambda \frac{1}{2}\|Rx\|_{\ell_2}^2\right\},$$

wherein x is the approximate impedance distribution, f is an operator calculating a set of simulated electrical signal parameters based on input x utilizing the physics-based simulation, y is a set of the respective electrical signal parameters, $l_2$ is a chosen norm, R is a regularization matrix, and λ is a chosen weight of the regularization or regularization parameter.

Clause 11: The measurement system of any one of clauses 1 to 10, wherein the plurality of electrical contacts are arranged on the tested material with symmetry about a symmetry of the material.

Clause 12: The measurement system of clause 11, wherein the symmetry of the tested material is a point, a line, a plane, a curve, or a manifold, and wherein a single mathematical operation made with reference to the symmetry maps each electrical contact of the plurality of electrical contacts to another electrical contact of the plurality of electrical contacts.

Clause 13: The measurement system of any one of clauses 1 to 12, wherein the electrical signal comprises a voltage signal.

Clause 14: The measurement system of any one of clauses 1 to 13, wherein the respective electrical signal parameters comprise respective current amplitudes.

Clause 15: The measurement system of any one of clauses 1 to 14, further comprising an input switch array electrically connected between the voltage source and the plurality of electrical contacts, wherein the input switch array comprises at least one input and at least N outputs, wherein the plurality of electrical contacts comprises N electrical contacts, and wherein the control module is configured to control the input switch array.

Clause 16: The measurement system of any one of clauses 1 to 15, further comprising measurement circuitry and an output switch array electrically connected between the plurality of respective resistors and the measurement circuitry, wherein the output switch array comprises at least one output and at least N+1 inputs, wherein the plurality of electrical contacts comprises N electrical contacts, and wherein the control module is configured to control the output switch array.

Clause 17: The measurement system of any one of clauses 1 to 16, wherein the measurement circuitry comprises an analog-to-digital converter, and wherein the control module controls the analog-to-digital converter to measure the respective electrical signal parameter at each respective resistor associated with each extraction electrical contact.

Clause 18: The measurement system of claim 17, further comprising a summing resistor connected between the common node and the return node, wherein the control module is further configured to: cause the input switch array to connect a first electrical contact from the plurality of electrical contacts to the electrical signal source as the input electrical contact; cause the analog-to-digital converter to measure a respective voltage drop across each of the respective resistors associated with the respective extraction electrical contacts; cause the analog-to-digital converter to measure a reference voltage associated with the common node; and determine a respective ratio based on each respective voltage drop and the reference voltage drop; and determine whether the tested material includes a crack or other defect based on the respective ratios.

Clause 19. A method including: causing, by a control module, an electrical signal source to be electrically connected to a selected electrical contact of a plurality of electrical contacts as an input electrical contact. The remaining electrical contacts of the plurality of electrical contacts are electrically connected to a return node of the electrical signal source as extraction electrical contacts. The method also may include causing, by the control module, the electrical signal source to output an electrical signal to the input electrical contact and causing, by the control module, a respective electrical signal parameter to be determined at a respective resistor associated with each respective extraction electrical contact. The respective resistors are electrically connected to a common node that is between the respective resistors and the return node. The method further may include determining, by the control module, whether the tested material includes a crack or other defect based on the respective electrical signal parameters.

Clause 20: The method of clause 19, further comprising: causing, by the control module, a reference electrical signal parameter to be determined at the common node; determining, by the control module, a respective electrical signal parameter ratio between each respective electrical signal parameter and the reference electrical signal parameter; and wherein determining whether the tested material includes a crack or other defect based on the respective electrical signal parameters comprises determining, by the control module, whether the tested material includes a crack or other defect based on the respective electrical signal parameter ratios.

Clause 21: The method of clause 20, wherein determining whether the tested material includes a crack or other defect based on the respective electrical signal parameter ratios comprises: comparing at least one of the respective electrical signal parameter ratios to a corresponding control electrical signal parameter ratio, wherein the control electrical signal parameter ratio is associated with the same input electrical contact and the same extraction electrical contact.

Clause 22: The method of clause 20, wherein determining whether the tested material includes a crack or other defect based on the respective electrical signal parameter ratios comprises: determining a first ratio between a first electrical signal parameter ratio and a second electrical signal parameter ratio; and comparing the first ratio to a control ratio, wherein the control ratio is associated with the same input electrical contact and the same extraction electrical contacts with which the first electrical signal parameter and the second electrical signal parameter are associated.

Clause 23: The method of clause 19, wherein determining whether the tested material includes a crack or other defect based on the respective electrical signal parameters comprises: comparing, by the control module, at least one of the respective electrical signal parameters to a corresponding control electrical signal parameter, wherein the control electrical signal parameter is associated with the same input electrical contact and the same extraction electrical contact.

Clause 24: The method of clause 19, wherein determining whether the tested material includes a crack or other defect based on the respective electrical signal parameters comprises: determining, by the control module, a first ratio between a first electrical signal parameter and a second electrical signal parameter; and comparing, by the control module, the first ratio to a control ratio, wherein the control ratio is associated with the same input electrical contact and the same extraction electrical contacts with which the first electrical signal parameter and the second electrical signal parameter are associated.

Clause 25: The method of clause 19, wherein determining whether the tested material includes a crack or other defect based on the respective electrical signal parameters comprises: calculating, by the control module, an approximate change in impedance distribution within the tested material based on a physics-based simulation, inputs representative of the electrical signal output to the input electrical contact, the respective electrical signal parameters, and respective control electrical signal parameters; and determining, by the control module, whether the material includes the crack or other defect based on the change in impedance distribution.

Clause 26: The method of clause 25, wherein calculating the approximate change in impedance distribution within the tested material comprises minimizing an output of an objective function:

$$\underset{x}{\operatorname{argmin}}\left\{F(x) := \frac{1}{2}\|f(x) - y\|_{\ell_2}^2 + \lambda \frac{1}{2}\|Rx\|_{\ell_2}^2\right\},$$

wherein x is the approximate change in impedance distribution, f is an operator calculating a set of simulated difference in electrical signal parameters based on input x utilizing the physics-based simulation, y is a set of differences between the respective electrical signal parameters and the respective control electrical signal parameters, $l_2$ is a chosen norm, R is a regularization matrix, and $\lambda$ is a chosen weight of the regularization or a regularization parameter.

Clause 27. The method of clause 19, wherein determining whether the tested material includes a crack or other defect based on the respective electrical signal parameters comprises: calculating, by the control module, an approximate impedance distribution within the tested material based on a physics-based simulation, inputs representative of the electrical signal output to the input electrical contact, and the respective electrical signal parameters; and determining, by the control module, whether the material includes the crack or other defect based on the approximate impedance distribution Clause 28: The method of clause 27, wherein calculating the approximate impedance distribution within the material comprises minimizing an output of an objective function:

$$\underset{x}{\operatorname{argmin}}\left\{F(x) := \frac{1}{2}\|f(x) - y\|_{\ell_2}^2 + \lambda \frac{1}{2}\|Rx\|_{\ell_2}^2\right\},$$

wherein x is the approximate impedance distribution, f is an operator calculating a set of simulated electrical signal parameters based on input x utilizing the physics-based simulation, y is a set of the respective electrical signal parameters, $l_2$ is a chosen norm, R is a regularization matrix, and $\lambda$ is a chosen weight of the regularization or regularization parameter.

Clause 29: The method of any one of clauses 19 to 28, wherein the plurality of electrical contacts are arranged on the tested material with symmetry about a symmetry of the material.

Clause 30: The method of clause 29, wherein the symmetry of the tested material is a point, a line, a plane, a curve, or a manifold, and wherein a single mathematical operation made with reference to the symmetry maps each electrical contact of the plurality of electrical contacts to another electrical contact of the plurality of electrical contacts.

Clause 31: The method of any one of clauses 19 to 30, wherein the respective electrical signal parameters comprise respective current amplitudes.

Clause 32: The method of any one of clauses 19 to 31, wherein an input switch array is electrically connected between the voltage source and the plurality of electrical contacts, wherein the input switch array comprises at least one input and at least N outputs, wherein the plurality of electrical contacts comprises N electrical contacts, and wherein the control module is configured to control the input switch array.

Clause 33: The method of any one of clauses 19 to 32, wherein an output switch array is electrically connected between the plurality of respective resistors and measurement circuitry, wherein the output switch array comprises at least one output and at least N+1 inputs, wherein the plurality of electrical contacts comprises N electrical contacts, and wherein the control module is configured to control the output switch array.

Clause 34: The method of clause 33, wherein: the measurement circuitry comprises an analog-to-digital converter; and causing the respective electrical signal parameter to be determined at the respective resistor associated with each respective extraction electrical contact comprises causing, by the control module, the analog-to-digital converter to measure the respective electrical signal parameter at each respective resistor associated with each extraction electrical contact.

Clause 35: The method of clause 34, wherein the control module is further configured to: cause the input switch array to connect a first electrical contact from the plurality of electrical contacts to the electrical signal source as the input electrical contact; cause the analog-to-digital converter to measure a respective voltage drop across each of the respective resistors associated with the respective extraction electrical contacts; cause the analog-to-digital converter to measure a reference voltage drop associated with the common node; determine a respective ratio based on each respective voltage drop and the reference voltage drop; and determine whether the tested material includes a crack or other defect based on the respective ratios.

Clause 36: A computer-readable medium comprising instructions that, when executed by one or more processors, causes the one or more processors to: cause an electrical signal source to be electrically connected to a selected electrical contact of a plurality of electrical contacts as an input electrical contact, wherein the remaining electrical contacts of the plurality of electrical contacts are electrically connected to a return node of the electrical signal source as extraction electrical contacts; cause the electrical signal source to output an electrical signal to the input electrical contact; cause a respective electrical signal parameter to be determined at a respective resistor associated with each respective extraction electrical contact, wherein the respective resistors are electrically connected to a common node that is between the respective resistors and the return node; and determine whether the tested material includes a crack or other defect based on the respective electrical signal parameters.

EXAMPLES

Example 1

Figure 9:
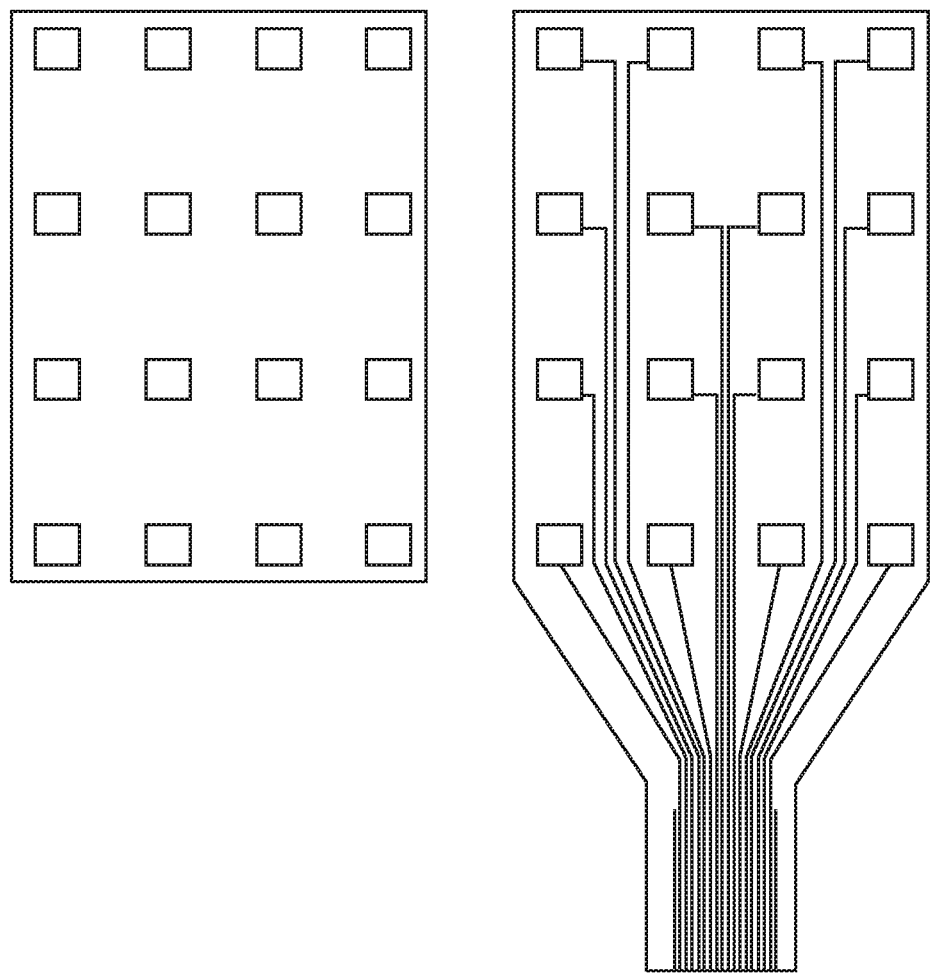
FIG. 9 is a drawing illustrating an example ceramic sample including a sixteen element electrical contact array and a flex circuit.
Figure 10:
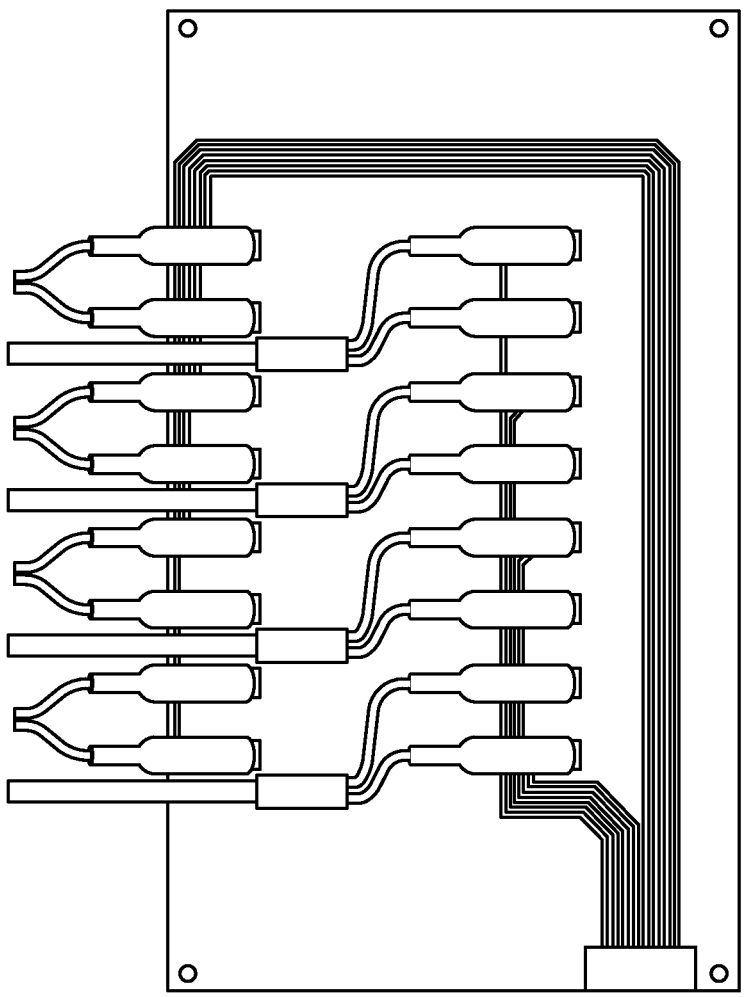
FIG. 10 is a drawing illustrating the example ceramic sample of FIG. 9 attached to a flex circuit, a breakout board, and a set of leads.
Figure 10:
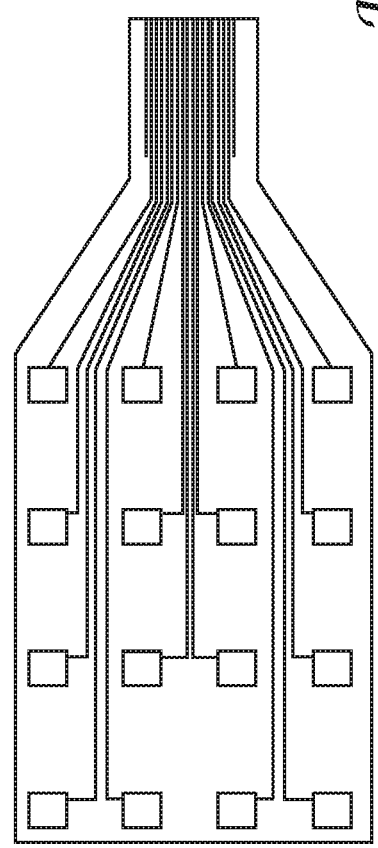

A ceramic sample included approximately 70% boron carbide and 30% silicon carbide. The back side of the ceramic sample was coated with a fiberglass/epoxy resin to keep the pieces in intimate contact after breaking. On the front side, sixteen approximately square electrical contacts were vapor deposited through a shadow mask. The electrical contacts included a first layer of titanium with a thickness of about 5 nanometers (nm) and a second layer of gold with a thickness of about 100 nm. A flex circuit was etched to match the locations of the electrical contacts, and a conductive silver-loaded epoxy was used to make electrical connections between the flex circuit and gold contacts. The flex circuit then was connected to a breakout board, which was connected to the switch matrixes. After the conductive epoxy was cured and the flex circuit attached to the electrical contacts, the ceramic sample was wrapped in tape to help further contain any pieces after breaking. FIG. 9 is a drawing illustrating the ceramic sample including the sixteen element electrical contact array and the flex circuit. FIG. 10 is a drawing illustrating an example ceramic material attached to a flex circuit, a breakout board, and a set of leads.

Various examples have been described. These and other examples are within the scope of the following claims.

What is claimed is:

1. A measurement system comprising:
   an electrical voltage source;
   a plurality of electrical contacts electrically coupled to a three-dimensional tested material such that the plurality of electrical contacts is arranged in a two-dimensional array along a surface of the three-dimensional tested material;
   a respective resistor associated with each electrical contact;
   a common resistor node, wherein each of the respective resistors is electrically connected to the common resistor node; and
   a control module communicatively coupled to the electrical voltage source, the control module being configured to:
   electrically connect the electrical voltage source to an input electrical contact selected from the plurality of electrical contacts, wherein all remaining electrical contacts of the plurality of electrical contacts other than the input electrical contact are electrically connected to a return node of the electrical voltage source as extraction electrical contacts;
   cause the electrical voltage source to output a voltage signal to the input electrical contact;
   measure a respective series resistor current at each respective resistor associated with each respective extraction electrical contact;
   measure a respective outbound current at each respective extraction electrical contact:
   calculate a respective ratio between a reference current and each respective outbound current measured across the two-dimensional array of extraction electrical contacts; and
   determine whether the three-dimensional tested material includes a defect based on at least one respective ratio of the respective ratios calculated between the reference current and each respective outbound current measured across the two-dimensional array of extraction electrical contacts.

2. The measurement system of claim 1, wherein the control module is further configured to determine the reference current by measuring a current at the input electrical contact.

3. The measurement system of claim 1, wherein the control module is further configured to determine the reference current based on a predetermined current associated with the three-dimensional tested material.

4. The measurement system of claim 1, wherein to determine whether the tested material includes the defect based on the at least one respective ratio, the control module is configured to:
   determine a ratio between a first respective ratio of the respective ratios and a second respective ratio of the respective ratios; and
   compare the ratio to a control ratio, wherein the control ratio is based on a current at the input electrical contact and same extraction electrical contacts with which the respective outbound currents are associated.

5. The measurement system of claim 1, wherein to determine whether the three-dimensional tested material includes the defect based on the at least one respective ratio, the control module is configured to compare at least one respective outbound current of the respective outbound currents to a control outbound current, wherein the control outbound current is associated with the input electrical contact and a same extraction electrical contact as the at least one respective outbound current.

6. The measurement system of claim 1, wherein the control module is further configured to calculate an impedance distribution change within the three-dimensional tested material based on a physics-based simulation, inputs representative of the voltage signal output by the electrical voltage source to the input electrical contact, the respective output currents, and respective control electrical outbound currents, and wherein to determine whether the three-dimensional tested material includes the defect based on the respective ratio, the control module is configured to determine whether the three-dimensional tested material includes the defect based on the impedance distribution change.

7. The measurement system of claim 6, wherein to calculate the impedance distribution change within the three-dimensional tested material, the control module is configured to minimize an output of an objective function described by:

$$\operatorname*{argmin}_{x}\left\{F(x) := \frac{1}{2}\|f(x) - y\|_{\ell_2}^2 + \lambda \frac{1}{2}\|Rx\|_{\ell_2}^2\right\},$$

where x is the impedance distribution change, f is an operator calculating a set of simulated difference in currents based on x utilizing the physics-based simulation, y is a set of differences between the respective outbound currents and the respective control electrical currents, $l_2$ is a chosen norm, R is a regularization matrix, and λ is a chosen weight of the regularization or a regularization parameter.

8. The measurement system of claim 7, wherein the control module is further configured to retrieve a value of x from a non-volatile memory (NVM) device attached to the three-dimensional tested material.

9. The measurement system of claim 1, wherein to determine whether the three-dimensional tested material includes the defect based on the respective ratio, the control module is configured to calculate an approximate impedance distribution within the three-dimensional tested material based on a physics-based simulation, inputs representative of the voltage signal output by the electrical voltage source to the input electrical contact, and the respective outbound currents, and to determine whether the three-dimensional tested material includes the defect based on the approximate impedance distribution.

10. The system of claim 9, wherein to calculate the approximate impedance distribution within the three-dimensional tested material, the control module is configured to minimize an output of an objective function described by:

$$\operatorname*{argmin}_{x}\left\{F(x) := \frac{1}{2}\|f(x) - y\|_{\ell_2}^2 + \lambda \frac{1}{2}\|Rx\|_{\ell_2}^2\right\},$$

where x is the approximate impedance distribution, f is an operator calculating a set of simulated currents based on x utilizing the physics-based simulation, y is a set of the respective currents, $l_2$ is a chosen norm, R is a regularization matrix, and $\lambda$ is a chosen weight of the regularization or regularization parameter.

11. The measurement system of claim 10, wherein the control module is further configured to retrieve a value of x from a non-volatile memory (NVM) device attached to the three-dimensional tested material.

12. The measurement system of claim 1, wherein the input electrical contact and the two-dimensional array of extraction electrical contacts are arranged on the three-dimensional tested material with symmetry about a symmetry of the three-dimensional tested material.

13. The measurement system of claim 12, wherein the symmetry of the three-dimensional tested material is described by one of a point, a line, a plane, a curve, or a manifold, and wherein a single mathematical operation made with reference to the symmetry maps each electrical contact of the plurality of electrical contacts to another electrical contact of the plurality of electrical contacts.

14. The measurement system of claim 12, wherein each respective electrical contact of the plurality of electrical contacts is positioned approximately opposite the symmetry of the three-dimensional tested material with reference to a corresponding position of a different electrical contact of the plurality of electrical contacts.

15. The measurement system of claim 1, wherein the defect comprises a crack in the three-dimensional tested material.

16. The measurement system of claim 1, wherein to determine the respective outbound currents, the control module is configured to determine respective amplitudes of the respective outbound currents.

17. The measurement system of claim 1, further comprising an analog-to-digital converter (ADC) coupled to the control module and to each respective electrical contact of the plurality of electrical contacts arranged in the two-dimensional array along the surface of the tested material, wherein to measure the respective outbound current at each respective extraction electrical contact the control module is configured to measure each respective outbound current using the ADC.

* * * * *

UNITED STATES PATENT AND TRADEMARK OFFICE
CERTIFICATE OF CORRECTION

PATENT NO. : 11,150,209 B2
APPLICATION NO. : 16/626264
DATED : October 19, 2021
INVENTOR(S) : Christopher Yungers et al.

Page 1 of 1

It is certified that error appears in the above-identified patent and that said Letters Patent is hereby corrected as shown below:

In the Claims

<u>Column 31</u>
Line 18, In Claim 1, delete "contacts is" and insert -- contacts are --, therefor.

Signed and Sealed this
Twenty-sixth Day of April, 2022

Katherine Kelly Vidal
*Director of the United States Patent and Trademark Office*